United States Patent
Clark et al.

(10) Patent No.: US 12,318,108 B2
(45) Date of Patent: Jun. 3, 2025

(54) ULTRASONIC SURGICAL INSTRUMENT WITH A CLAMP ARM CLOCKING ASSEMBLY

(71) Applicant: Cilag GmbH International, Zug (CH)

(72) Inventors: Jeffrey L. Clark, Maineville, OH (US); Morgan R. Hunter, Cincinnati, OH (US); Brian D. Black, Loveland, OH (US); Thomas B. Remm, Milford, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/413,251

(22) Filed: Jan. 16, 2024

(65) Prior Publication Data

US 2024/0148402 A1 May 9, 2024

Related U.S. Application Data

(63) Continuation of application No. 17/128,275, filed on Dec. 21, 2020, now Pat. No. 11,911,064.

(51) Int. Cl.
*A61B 17/32* (2006.01)

(52) U.S. Cl.
CPC ........... *A61B 17/320092* (2013.01); *A61B 2017/320071* (2017.08); *A61B 2017/320074* (2017.08);
(Continued)

(58) Field of Classification Search
CPC .......... A61B 17/320092; A61B 2017/320071; A61B 2017/320074; A61B 2017/320094;
(Continued)

(56) References Cited

U.S. PATENT DOCUMENTS 7,354,440 B2   4/2008   Truckai et al.
7,381,209 B2   6/2008   Truckai et al.
(Continued)

FOREIGN PATENT DOCUMENTS

WO    WO 2019/018289 A1    1/2019

OTHER PUBLICATIONS

International Search Report and Written Opinion dated Feb. 28, 2022, for International Application No. PCT/IB2021/062028, 12 pages.
(Continued)

*Primary Examiner* — Brooke Labranche
(74) *Attorney, Agent, or Firm* — Frost Brown Todd LLP

(57) ABSTRACT

A surgical instrument includes an end effector having a clamp arm pivotable relative to an ultrasonic blade, an articulation section configured to deflect the end effector, an acoustic waveguide having a distal portion extending along an axis, a clamp arm closure assembly comprising a body configured to actuate in order to drive the pivoting of the clamp arm, and a clamp arm clocking assembly. The clamp arm clocking assembly is capable of driving rotation of the clamp arm about the axis relative to the ultrasonic blade between a first clocked position and a second clocked position. The clamp arm clocking assembly includes a rotating body pivotally coupled with the clamp arm, a translating drive extending through the articulation section, and a rotation driver assembly. The rotation driver is in communication with the translating driver to convert translational motion of the translating driver into rotational motion of the rotating body.

20 Claims, 23 Drawing Sheets

(52) U.S. Cl.
CPC .............. *A61B 2017/320093* (2017.08); *A61B 2017/320094* (2017.08); *A61B 2017/320095* (2017.08)

(58) Field of Classification Search
CPC ........... A61B 2017/320095; A61B 2017/2929; A61B 2017/2943
See application file for complete search history.

(56) References Cited

U.S. PATENT DOCUMENTS

| | | |
|---|---|---|
| 8,663,220 B2 | 3/2014 | Wiener et al. |
| 9,095,367 B2 | 8/2015 | Olson et al. |
| 9,393,037 B2 | 7/2016 | Olson et al. |
| 9,402,682 B2 | 8/2016 | Worrell et al. |
| 9,949,785 B2 | 4/2018 | Price et al. |
| 10,034,683 B2 | 7/2018 | Monroe et al. |
| 10,413,291 B2 | 9/2019 | Worthington et al. |
| 11,806,037 B2 | 11/2023 | Black et al. |
| 2006/0079874 A1 | 4/2006 | Faller et al. |
| 2007/0191713 A1 | 8/2007 | Eichmann et al. |
| 2008/0039255 A1 | 2/2008 | Jinno et al. |
| 2008/0200940 A1 | 8/2008 | Eichmann et al. |
| 2011/0087212 A1 | 4/2011 | Aldridge et al. |
| 2019/0021752 A1 | 1/2019 | Boudreaux |
| 2019/0380735 A1 | 12/2019 | Cuti et al. |
| 2021/0059707 A1 | 3/2021 | Hunter et al. |
| 2021/0059708 A1 | 3/2021 | Hunter et al. |
| 2021/0059709 A1 | 3/2021 | Black et al. |
| 2021/0059710 A1 | 3/2021 | Black et al. |
| 2021/0059711 A1 | 3/2021 | Hunter et al. |
| 2022/0125460 A1 | 4/2022 | Black et al. |
| 2022/0125463 A1 | 4/2022 | Black et al. |
| 2022/0125464 A1 | 4/2022 | Black et al. |
| 2022/0125465 A1 | 4/2022 | Beckman et al. |
| 2022/0125466 A1 | 4/2022 | Beckman et al. |
| 2022/0125467 A1 | 4/2022 | Black et al. |
| 2022/0125468 A1 | 4/2022 | Scheib et al. |
| 2022/0125469 A1 | 4/2022 | Black et al. |
| 2022/0125470 A1 | 4/2022 | Black et al. |
| 2022/0125471 A1 | 4/2022 | Black et al. |
| 2022/0125472 A1 | 4/2022 | Beckman et al. |
| 2022/0125473 A1 | 4/2022 | Black et al. |
| 2022/0192697 A1 | 6/2022 | Clark et al. |

OTHER PUBLICATIONS

U.S. Appl. No. 62/930,638, entitled "Articulation Joint with Helical Lumen," filed Nov. 5, 2019.

ULTRASONIC SURGICAL INSTRUMENT WITH A CLAMP ARM CLOCKING ASSEMBLY

PRIORITY

This application is a continuation of U.S. patent application Ser. No. 17/128,275, entitled "Ultrasonic Surgical Instrument with a Clamp Arm Clocking Assembly," filed Dec. 21, 2020, published as U.S. Pat. Pub. No. 2022/0192697 on Jun. 23, 2022, issued as 11,911,064 on Feb. 27, 2024.

BACKGROUND

A variety of surgical instruments include an end effector for use in conventional medical treatments and procedures conducted by a medical professional operator, as well as applications in robotically assisted surgeries. Such surgical instruments may be directly gripped and manipulated by a surgeon or incorporated into robotically assisted surgery. In the case of robotically assisted surgery, the surgeon may operate a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletol gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an ultrasonic blade, a tissue grasper, a needle driver, an electrosurgical cautery probes, etc. Each of these structures performs functions for the surgeon, for example, cutting tissue, coagulating tissue, holding or driving a needle, grasping a blood vessel, dissecting tissue, or cauterizing tissue.

In one example, the end effector of the surgical instrument includes a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure. The power level used to drive the blade element may be varied (e.g., in real time) based on sensed parameters such as tissue impedance, tissue temperature, tissue thickness, and/or other factors. Some instruments have a clamp arm and clamp pad for grasping tissue with the blade element. Examples of ultrasonic surgical instruments and related concepts are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; and U.S. Pub. No. 2008/0200940, entitled "Ultrasonic Device for Cutting and Coagulating," published Aug. 21, 2008, now abandoned, the disclosure of which is incorporated by reference herein.

Examples of robotic systems, at least some of which have ultrasonic features and/or associated articulatable portions, include U.S. patent application Ser. No. 16/556,661, entitled "Ultrasonic Surgical Instrument with a Multi-Planar Articulating Shaft Assembly," filed on Aug. 30, 2019, issued as U.S. Pat. No. 11,690,642 on Jul. 4, 2023; U.S. patent application Ser. No. 16/556,667, entitled "Ultrasonic Transducer Alignment of an Articulating Ultrasonic Surgical Instrument," filed on Aug. 30, 2019, issued as U.S. Pat. No. 11,612,409 on Mar. 28, 2023; U.S. patent application Ser. No. 16/556,625, entitled "Ultrasonic Surgical Instrument with Axisymmetric Clamping," filed on Aug. 30, 2019, issued as U.S. Pat. No. 11,471,181 on Oct. 18, 2022; U.S. patent application Ser. No. 16/556,635, entitled "Ultrasonic Blade and Clamp Arm Alignment Features," filed on Aug. 30, 2019, issued as U.S. Pat. No. 11,457,945 on Oct. 4, 2022; U.S. patent application Ser. No. 16/556,727, entitled "Rotatable Linear Actuation Mechanism," filed on Aug. 30, 2019, issued as U.S. Pat. No. 11,712,261 on Aug. 1, 2023; and/or U.S. Pat. App. No. 62/930,638, entitled "Articulation Joint with Helical Lumen," filed on Nov. 5, 2019. The disclosure of each of these applications is incorporated by reference herein.

Some instruments are operable to seal tissue by applying radiofrequency (RF) electrosurgical energy to the tissue. Examples of such devices and related concepts are disclosed in U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Some instruments are capable of applying both ultrasonic energy and RF electrosurgical energy to tissue. Examples of such instruments are described in U.S. Pat. No. 9,949,785, entitled "Ultrasonic Surgical Instrument with Electrosurgical Feature," issued Apr. 24, 2018, the disclosure of which is incorporated by reference herein; and U.S. Pat. No. 8,663,220, entitled "Ultrasonic Surgical Instruments," issued Mar. 4, 2014, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
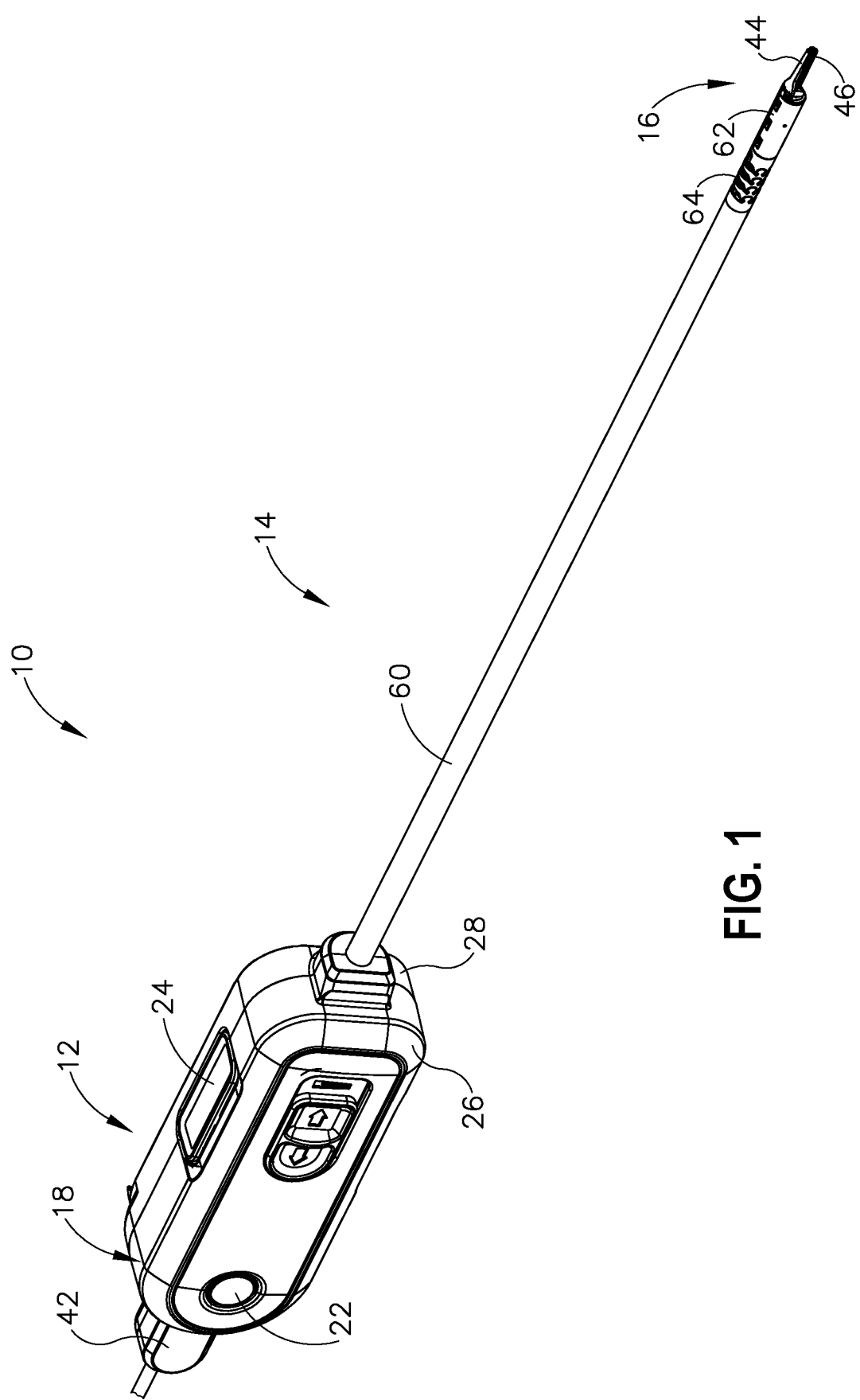
FIG. 1 depicts a front perspective view of a first example of an ultrasonic surgical instrument having a first end effector, a shaft assembly having a first distal shaft portion, and a base assembly configured to connect to a robotic driven interface.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "front," "rear," "clockwise," "counterclockwise," "longitudinal," and "transverse" also are used herein for reference to relative positions and directions. Such terms are used below with reference to views as illustrated for clarity and are not intended to limit the invention described herein.

I. Exemplary Surgical Instrument

FIG. 1 shows an exemplary surgical instrument, such as a first example of an ultrasonic surgical instrument (10). At least part of ultrasonic surgical instrument (10) may be constructed and operable in accordance with at least some of the teachings of any of the various patents, patent application publications, and patent applications that are cited herein. As described therein and as will be described in greater detail below, ultrasonic surgical instrument (10) is operable to cut tissue and seal or weld tissue (e.g., a blood vessel, etc.) substantially simultaneously. While the present example incorporates various ultrasonic features as ultrasonic surgical instrument (10), the invention is not intended to be unnecessarily limited to the ultrasonic features described herein.

Ultrasonic surgical instrument (10) of the present example comprises a body assembly, such as a base assembly (12), a shaft assembly (14), and an end effector (16). Base assembly (12) includes a housing (18), a button (22), and a pair of latch clasps (24). Button (22) is operatively connected to an electrical base power controller (not shown) and configured to selectively power ultrasonic surgical instrument (10) for use. In addition, housing (18) of the present example includes a front housing cover (26) and a rear housing cover (28) removably secured together via latch clasps (24). More particularly, latch clasps (24) removably secure front housing cover (26) to rear housing cover (28) such that front housing cover (26) may be removed for accessing an interior space (30) (see FIG. 5) within base assembly (12). Shaft assembly (14) distally extends from base assembly (12) to end effector (16) to thereby communicate mechanical and/or electrical forces therebetween for use as will be discussed below in greater detail. As shown in the present example, base assembly (12) is configured to operatively connect to a robotic drive (not shown) for driving various features of shaft assembly (14) and/or end effector (16). However, in another example, body assembly may alternatively include a handle assembly (not shown), which may include a pistol grip (not shown) in one example, configured to be directly gripped and manipulated by the surgeon for driving various features of shaft assembly (14) and/or end effector (16). The invention is thus not intended to be unnecessarily limited to use with base assembly (12) and the robotic drive (not shown).

Figure 2:
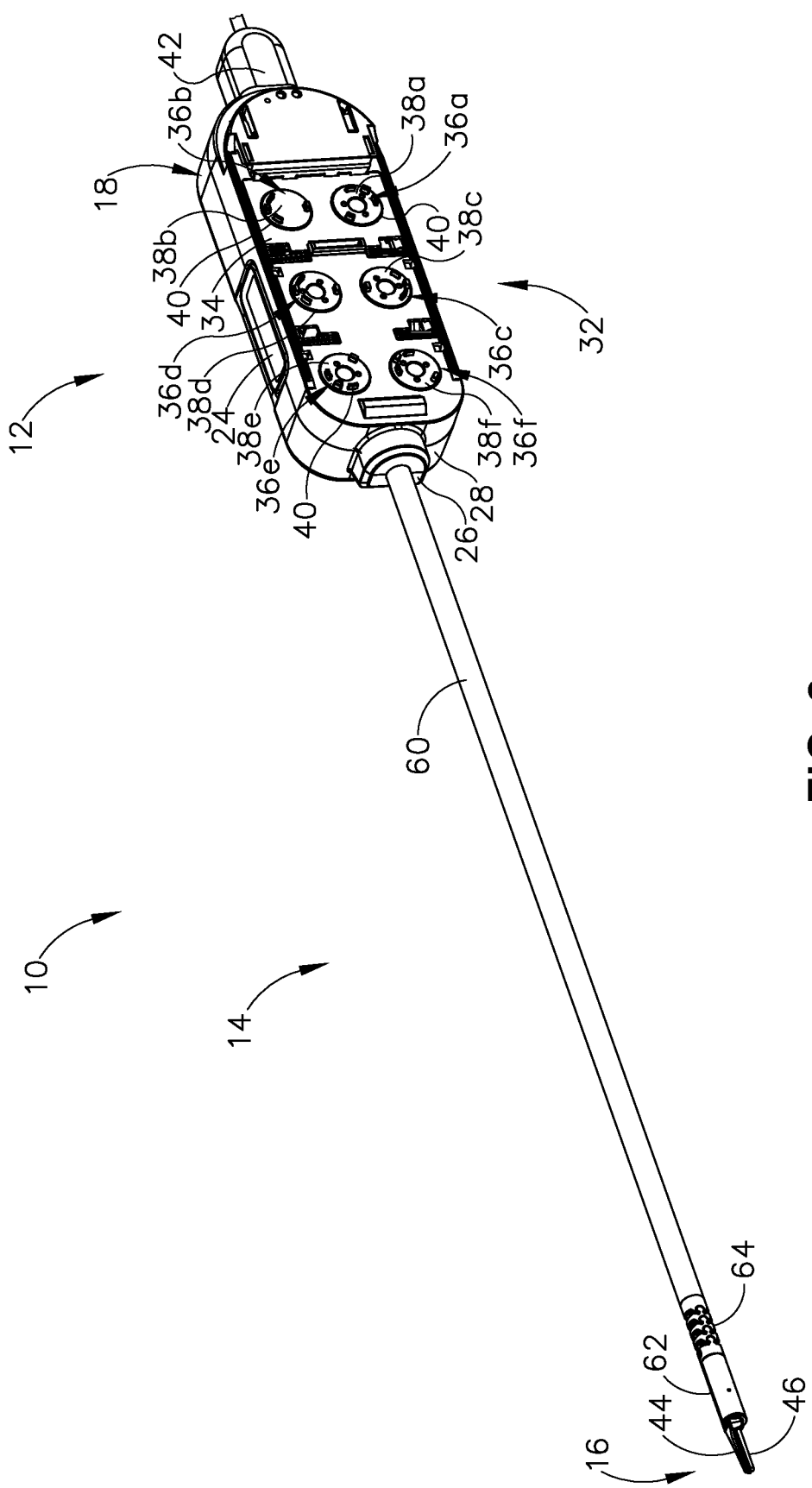
FIG. 2 depicts a rear perspective view of the ultrasonic surgical instrument of FIG. 1.

To this end, with respect to FIG. 2, base assembly (12) includes a robotic driven interface (32) extending through a base plate (34) of rear housing cover (28) and configured to mechanically couple with the robotic drive (not shown). Robotic driven interface (32) of the present example includes a plurality of instrument actuators (36a, 36b, 36c, 36d, 36e, 36f) having a plurality of input bodies (38a, 38b, 38c, 38d, 38e, 380, respectively. Each input body (38a, 38b, 38c, 38d, 38e, 38f), which may also be referred to herein as a "puck," is configured to removably connect with the robotic drive (not shown) and, in the present example, is generally cylindrical and rotatable about an axis. Input bodies (38a, 38b, 38c, 38d, 38e, 380 have a plurality of slots (40) configured to receive portions of the robotic drive (not shown) for gripping and rotatably driving input bodies (38a, 38b, 38c, 38d, 38e, 380 in order to direct operation of shaft assembly (14) and/or end effector (16) as will be discussed below in greater detail. Base assembly (12) also receives an electrical plug (42) operatively connected to an electrical power source (not shown) to provide electrical power to base assembly (12) for operation as desired, such as powering electrical base power controller (not shown) and directing electrical energy to various features of shaft assembly (14) or end effector (16) associated with cutting, sealing, or welding tissue.

A. Exemplary End Effector and Acoustic Drivetrain

Figure 3A:
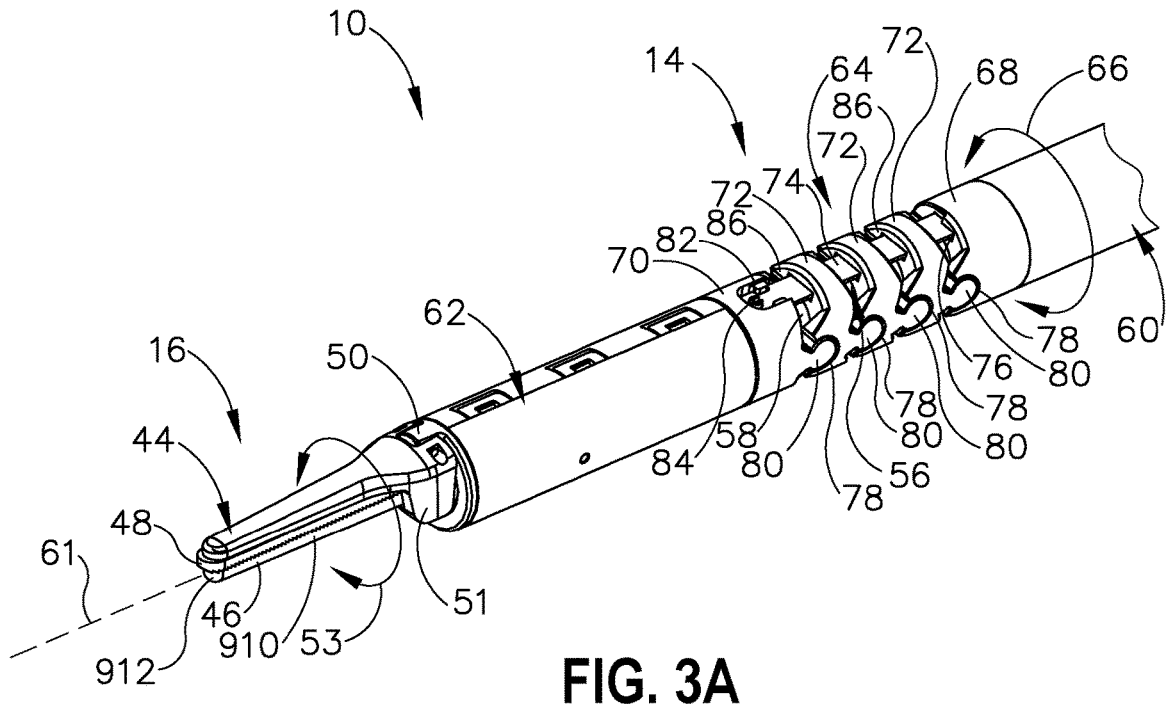
FIG. 3A depicts an enlarged perspective view of the ultrasonic surgical instrument of FIG. 1 with the end effector in a closed position and the shaft assembly in a straight configuration.
Figure 3B:
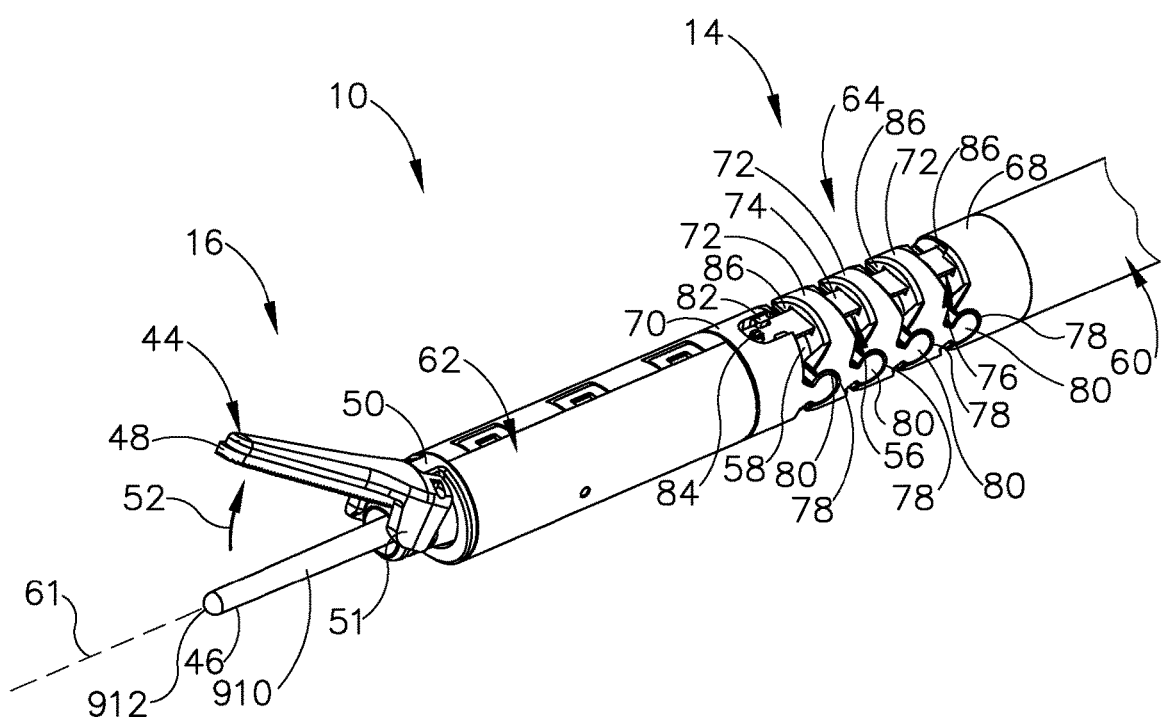
FIG. 3B depicts the enlarged perspective view of the ultrasonic surgical instrument similar to FIG. 3A, but showing the end effector in an open position.

As best seen in FIGS. 3A-3B, end effector (16) of the present example includes a clamp arm (44) and an ultrasonic blade (46). Clamp arm (44) has a clamp pad (48) secured to an underside of clamp arm (44), facing blade (46). In one example, clamp pad (48) may comprise polytetrafluoroethylene (PTFE) and/or any other suitable material(s). Clamp arm (44) is pivotally secured to a distally projecting tongue (50) of shaft assembly (14). Clamp arm (44) is operable to selectively pivot toward and away from blade (46) to selectively clamp tissue between clamp arm (44) and blade (46). A pair of arms (51) extend transversely from clamp arm (44) and are pivotally secured to another portion of shaft assembly (14) configured to longitudinally slide to pivot clamp arm (44) as indicated by an arrow (52) between a closed position shown in FIG. 3A and an open position shown in FIG. 3B.

In addition to pivoting relative to blade (46), clamp arm (44) of the present example is further configured to rotate about blade (46) relative to blade (46) and also relative to shaft assembly (14) as indicated by an arrow (53). In one example, clamp arm (44) rotates in the clockwise or counterclockwise directions completely around blade (46) and may be selectively fixed in any angular position relative to blade (46) for directing clamp arm (44) from the open position to the closed position for clamping tissue. In another example, clamp arm (44) may have rotational stops (not shown) configured to limit rotational movement of clamp arm (44) relative to blade (46) in one or more predetermined positions.

Blade (46) of the present example is operable to vibrate at ultrasonic frequencies in order to effectively cut through and seal tissue, particularly when the tissue is being compressed between clamp pad (48) and blade (46). Blade (46) is positioned at a distal end of an acoustic drivetrain. This acoustic drivetrain includes a transducer assembly (54) (see FIG. 5) and an acoustic waveguide (56), which includes a flexible portion (58) discussed below in greater detail. It should be understood that waveguide (56) may be configured to amplify mechanical vibrations transmitted through waveguide (56). Furthermore, waveguide (56) may include features operable to control the gain of the longitudinal vibrations along waveguide (56) and/or features to tune waveguide (56) to the resonant frequency of the system. Various suitable ways in which waveguide (56) may be mechanically and acoustically coupled with transducer assembly (54) (see FIG. 5) will be apparent to those of ordinary skill in the art in view of the teachings herein.

Those of ordinary skill in the art will understand that, as a matter of physics, a distal end of blade (46) is located at a position corresponding to an anti-node associated with resonant ultrasonic vibrations communicated through flexible portion (58) of waveguide (56). When transducer assembly (54) (see FIG. 5) is energized, the distal end of blade (46) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (54) (see FIG. 5) of the present example is activated, these mechanical oscillations are transmitted through waveguide (56) to reach blade (46), thereby providing oscillation of blade (46) at the resonant ultrasonic frequency. Thus, when tissue is secured between blade (46) and clamp pad (48), the ultrasonic oscillation of blade (46) may simultaneously sever the tissue and denature the proteins in adjacent tissue cells, thereby providing a coagulative effect with relatively little thermal spread. In some versions, end effector (16) is operable to apply radiofrequency (RF) electrosurgical energy to tissue in addition to applying ultrasonic energy to tissue. In any case, other suitable configurations for an acoustic transmission assembly and transducer assembly (54) will be apparent to one of ordinary skill in the art in view of the teachings herein. Similarly, other suitable configurations for end effector (16) will be apparent to those of ordinary skill in the art in view of the teachings herein.

B. Exemplary Shaft Assembly and Articulation Section

As shown in FIGS. 3A-3B, shaft assembly (14) includes a proximal shaft portion (60) extending along a longitudinal axis (61), a first distal shaft portion (62) distally projecting relative to the proximal shaft portion (60), and an articulation section (64) extending between proximal and distal shaft portions (60, 62). Shaft assembly (14) is configured to rotate about longitudinal axis (61) as indicated by an arrow (66). In one example, shaft assembly (14) rotates in the clockwise or counterclockwise directions completely around longitudinal axis (61) and may be selectively fixed in any rotational position about longitudinal axis (61) for positioning articulation section (64) and/or end effector (16) about longitudinal axis (61). While end effector (16) generally rotates with shaft assembly (14) as indicated by arrow (66), end effector (16) may be simultaneously and independently rotated as indicated by arrow (53) relative to shaft assembly (14) during use for repositioning portions of shaft assembly (14) and/or end effector (16) as desired.

Articulation section (64) is configured to selectively position end effector (16) at various lateral deflection angles relative to longitudinal axis (61) defined by proximal shaft portion (60). Articulation section (64) may take a variety of forms. In the present example, articulation section (64) includes a proximal link (68), a distal link (70), and a plurality of intermediate links (72) connected in series between proximal and distal links (68, 70). Articulation section (64) further includes a pair of articulation bands (74) extending along a pair of respective channels (76) collectively defined through links (68, 70, 72). Links (68, 70, 72) are generally configured to pivot relative to each other upon actuation of articulation bands (74) to thereby bend articulation section (64) with flexible portion (58) of waveguide (56) therein to achieve an articulated state. By way of example only, articulation section (64) may alternatively or additionally be configured in accordance with one or more teachings of U.S. Pat. No. 9,402,682, entitled "Articulation Joint Features for Articulating Surgical Device," issued Aug. 2, 2016, the disclosure of which is incorporated by reference herein. As another merely illustrative example, articulation section (64) may alternatively or additionally be configured in accordance with one or more teachings of U.S. Pat. No. 9,393,037, issued Jul. 19, 2016, entitled "Surgical Instruments with Articulating Shafts," the disclosure of which is incorporated by reference herein and U.S. Pat. No. 9,095,367, issued Aug. 4, 2015, entitled "Flexible Harmonic Waveguides/Blades for Surgical Instruments," the disclosure of which is incorporated by reference herein. In addition to or in lieu of the foregoing, articulation section (64) and/or may be constructed and/or operable in accordance with at least some of the teachings of U.S. Pat. No. 10,034,683, entitled "Ultrasonic Surgical Instrument with Rigidizing Articulation Drive Members," issued on Jul. 31, 2018. Alternatively, articulation section (64) may be constructed and/or operable in any other suitable fashion.

Links (68, 70, 72) shown in FIGS. 3B-4B pivotally interlock to secure distal shaft portion (62) relative to proximal shaft portion (60) while allowing for deflection of distal shaft portion (62) relative to longitudinal axis (61). In the present example, proximal link (68) is rigidly connected to proximal shaft portion (60) and has a pair of arcuate grooves (78) opposed from each other. Intermediate links (72) respectively have a pair of arcuate tongues (80) proximally extending therefrom and a pair of arcuate grooves (78) positioned distally opposite from respective tongues (80). Each intermediate link (72) has tongues (80) pivotally received within adjacent arcuate grooves (78) of another intermediate link (72) or proximal link (68) as applicable. Distal link (70) is rigidly connected to distal shaft portion (62) and has another pair of arcuate tongues (80) opposed from each other and pivotally received within adjacent arcuate grooves (78) of intermediate link (72). Tongues (80) and grooves (78) connect together to form the series of interlocked links (68, 70, 72).

Figure 4A:
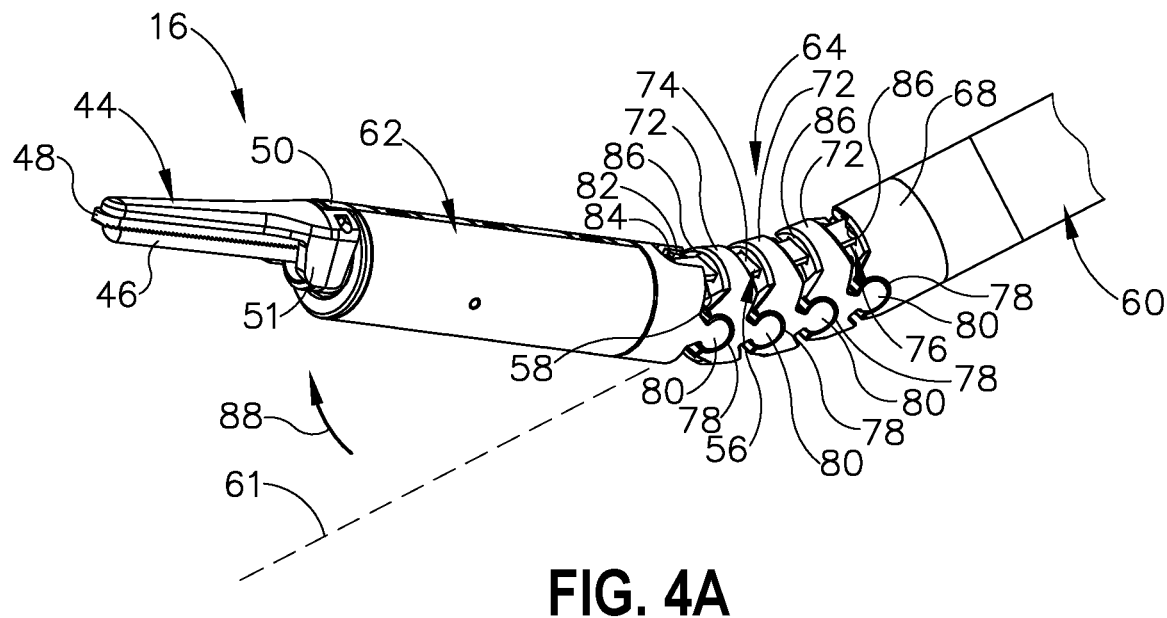
FIG. 4A depicts an enlarged perspective view of the ultrasonic surgical instrument of FIG. 1 with the end effector in a closed position and the shaft assembly in a first articulated configuration.
Figure 4B:
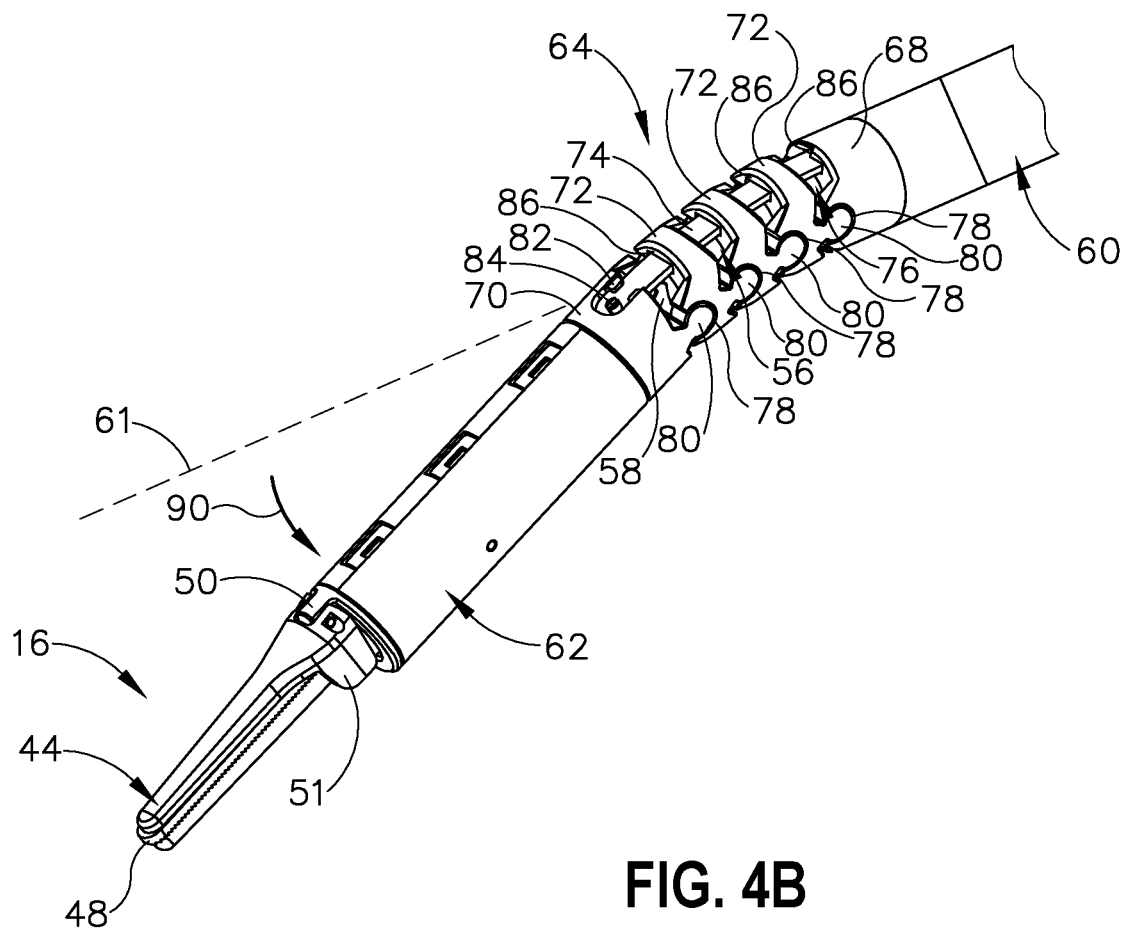
FIG. 4B depicts the enlarged perspective view of the ultrasonic surgical instrument similar to FIG. 4A, but with the shaft assembly in a second articulated configuration.

Distal link (70) further includes a pair of opposing notches (82) with a pin (84) therein configured to receive distal end portions of respective articulation bands (74). More particularly, pins (84) extend through a hole in each respective articulation bands (74) while distal end portions of respective articulation bands (74) are coupled within notches (82). Slots (86) in each of intermediate and proximal links (72, 68) longitudinally align with each other and notches (82) to collectively define channels (76) configured to receive articulation bands (74) while allowing articulation bands (74) to slide relative to links (68, 70, 72). To this end, when articulation bands (74) translate longitudinally in an opposing fashion, this will cause articulation section (64) to bend, thereby laterally deflecting end effector (16) away from the longitudinal axis (61) of proximal shaft portion (60) from a straight configuration as shown in FIG. 3B to a first articulated configuration as shown in FIG. 4A and indicated by an arrow (88) or a second articulated configuration as shown in FIG. 4B and indicated by an arrow (90). In particular, end effector (16) will be articulated toward the articulation band (74) that is being pulled proximally. During such articulation, the other articulation band (74) may be pulled distally. Alternatively, the other articulation band (74) may be driven distally by an articulation control. Furthermore, flexible acoustic waveguide (56) is configured to effectively communicate ultrasonic vibrations from waveguide (56) to blade (46) even when articulation section (64) is in an articulated configuration as shown in FIGS. 4A-4B.

C. Exemplary Base Assembly with Instrument Actuators for Robotic Interface

Figure 5:
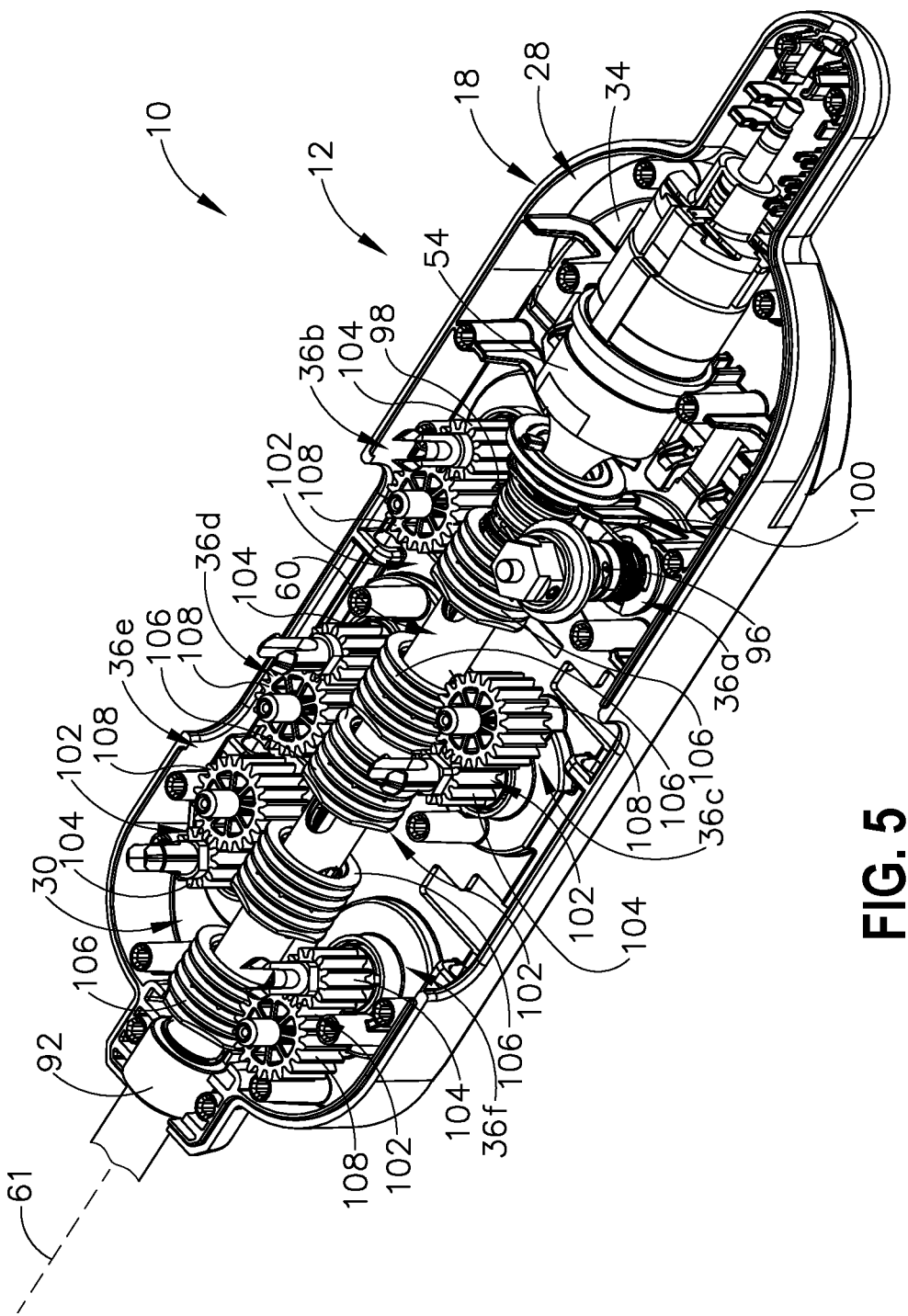
FIG. 5 depicts an enlarged perspective view of the ultrasonic surgical instrument of FIG. 1 with the base assembly having various components removed for greater clarity of an interior space of the base assembly.

FIG. 5 shows interior space (30) of base assembly (12) with instrument actuators (36a, 36b, 36c, 36d, 36e, 36f) in greater detail. Generally, instrument actuators (36a, 36b, 36c, 36d, 36e, 36f) are engaged with shaft assembly (14) and configured to direct movement of end effector (16) and/or shaft assembly (14), such as movement indicated above in one example by arrows (52, 53, 66, 88, 90) (see FIGS. 3A-4B). Shaft assembly (14) is received within base assembly (12) and supported by bearings (92) therein to operatively connect each respective instrument actuator (36a, 36b, 36c, 36d, 36e, 36f) to shaft assembly (14) as well as operatively connect acoustic waveguide (56) (see FIG. 3A) to transducer assembly (54) and a generator (not shown) of the acoustic drivetrain. More particularly, transducer assembly (54) is coupled with generator (not shown) such that transducer assembly (54) receives electrical power from generator (not shown). Piezoelectric elements (not shown) in transducer assembly (54) convert that electrical power into ultrasonic vibrations. Generator (not shown) may be coupled to the electrical power source (not shown) via electrical plug (42) (see FIG. 1) and a control module (not shown) that are configured to provide a power profile to transducer assembly (54) that is particularly suited for the generation of ultrasonic vibrations through transducer assembly (54). By way of example only, generator (not shown) may comprise a GEN04 or GEN11 sold by Ethicon Endo-Surgery, Inc. of Cincinnati, Ohio. In addition or in the alternative, generator (not shown) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. Still other suitable forms that generator (not shown) may take, as well as various features and operabilities that generator (not shown) may provide, will be apparent to those of ordinary skill in the art in view of the teachings herein.

Figure 6:
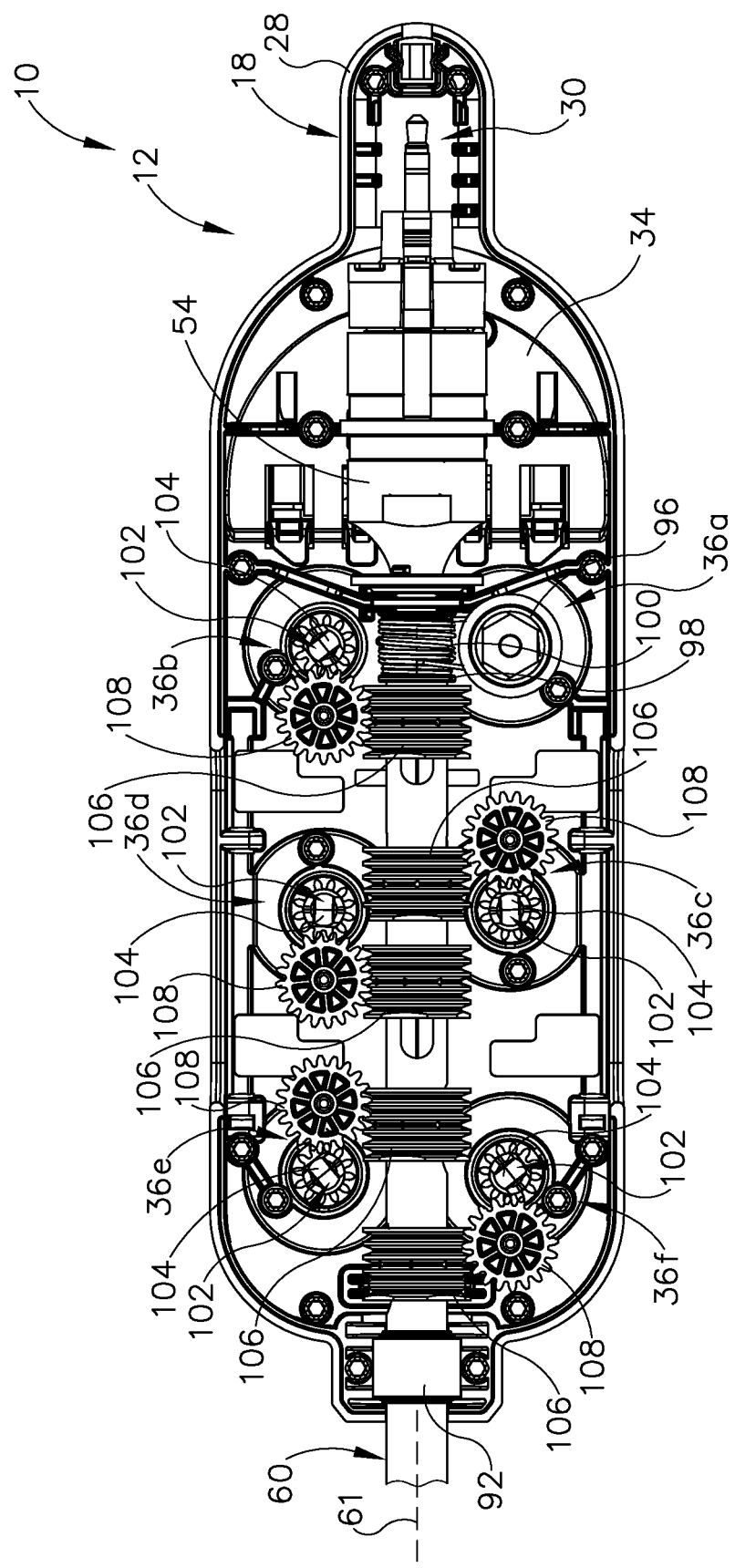
FIG. 6 depicts an enlarged front view of the ultrasonic surgical instrument of FIG. 1 with the base assembly having various components removed for greater clarity of the interior space of the base assembly.

The present example of base assembly (12) shown in FIGS. 5-6 includes six instrument actuators (36a, 36b, 36c, 36d, 36e, 36f), although it will be appreciated that any such number of such instrument actuators (36a, 36b, 36c, 36d, 36e, 36f) configured to direct movement of shaft assembly (14) and/or end effector (16) may be similarly used. As shown with respect to operation of ultrasonic surgical instrument (10), instrument actuator (36a) is more particularly a roll system actuator (36a) configured to rotate shaft assembly (14) about longitudinal axis (61). In contrast, instrument actuators (36b, 36c, 36d, 36e, 36f) are linear system actuators (36b, 36c, 36d, 36e, 36f) configured to translationally drive movement of portions of end effector (16) and/or shaft assembly (14) while simultaneously allowing for rotation of shaft assembly (14) via roll system actuator (36a).

Roll system actuator (36a) in one example includes a drive spool (96) rigidly connected to puck (38a) (see FIG. 2) and a driven spool (98) rigidly connected to proximal shaft portion (60) within housing (18). Drive spool (96) is mounted to rotate with puck (38a) (see FIG. 2) about a common puck axis, whereas driven spool (98) is mounted to rotate with proximal shaft portion (60) about the longitudinal axis (61). A cable (100) wraps around each of the drive and driven spools (96, 98), accommodating the differing orientation of the puck axis and longitudinal axis (61), such that rotating drive spool (96) via puck (38a) (see FIG. 2) urges rotation of driven spool (98). In turn, shaft assembly (14), including proximal and distal shaft portions (60, 62) rotates about longitudinal axis (61) as indicated by arrow (66) (see FIG. 3A), such as by robotically driven actuation of puck (38a) (see FIG. 2).

Linear system actuators (36b, 36c, 36d, 36e, 36f) of the present example include a gear-rack mechanism (102) having a rotatable drive gear (104), a translatable rack gear (106), and an idler gear (108) connected therebetween. Drive gears (104) are respectively connected to and rigidly project from pucks (38b, 38c, 38d, 38e, 38f) (see FIG. 2), whereas each rack gear (106) is connected to another portion of proximal shaft portion (60) directing movement of shaft assembly (14) and/or end effector (16) as discussed above. Each rack gear (106) is cylindrical and rigidly connected relative to proximal shaft portion (60) to rotate therewith. Rack gear (106) is thereby configured to rotate with shaft assembly (14) while remaining meshed with idler gear (108). Rotating respective pucks (38b, 38c, 38d, 38e, 38f) (see FIG. 2) thus respectively rotates drive gears (104) and idler gears (108) to translate rack gears (106) as desired.

In the present example, with respect to FIGS. 2-4B and FIG. 6, linear system actuator (36b) has puck (38b) operatively connected to clamp arm (44) to direct movement of clamp arm (44) between the open and closed positions according to arrow (52). Linear systems (36c, 36d) have respective pucks (38c, 38d) operatively connected to clamp arm (44) to direct movement of clamp arm (44) around blade (46) in both the clockwise and counterclockwise directions according to arrow (53). In addition, linear system actuators (36e, 36f) have respective pucks (38e, 38f) operatively connected to articulation bands (74) to direct movement of articulation section (64) according to arrows (88, 90) for deflecting end effector (16) relative to longitudinal axis (61). Of course, in other examples, instrument actuators (36a, 36b, 36c, 36d, 36e, 36f) may be alternatively configured with more or less actuators (36a, 36b, 36c, 36d, 36e, 36f) and/or more or less movement as desired. The invention is thus not intended to be unnecessarily limited to instrument actuators (36a, 36b, 36c, 36d, 36e, 36f) or particular movements of shaft assembly (14) and/or end effector (16) as described in the present example.

II. Exemplary End Effector with Clamp Arm Clocking Assembly

As mentioned above, articulation bands (74) are configured to drive articulation section (64) according to arrows (88, 90) for deflecting end effector (16) relative to longitudinal axis (61). Additionally, clamp arm (44) is configured to rotate relative to blade (46), as indicated by arrow (53) (i.e., clocking clamp arm (44)), into various clocked positions relative to blade (46); as well as pivot, as indicated by arrow (52), between an open position and closed position in order to engage tissue. Therefore, in exemplary use, it may be desirable to articulate end effector (16) and clock clamp arm (44) relative to blade (46) into a desired position adjacent to targeted tissue, and then grasp tissue by pivoting clamp arm (44) toward and away from blade (46).

Figure 7:
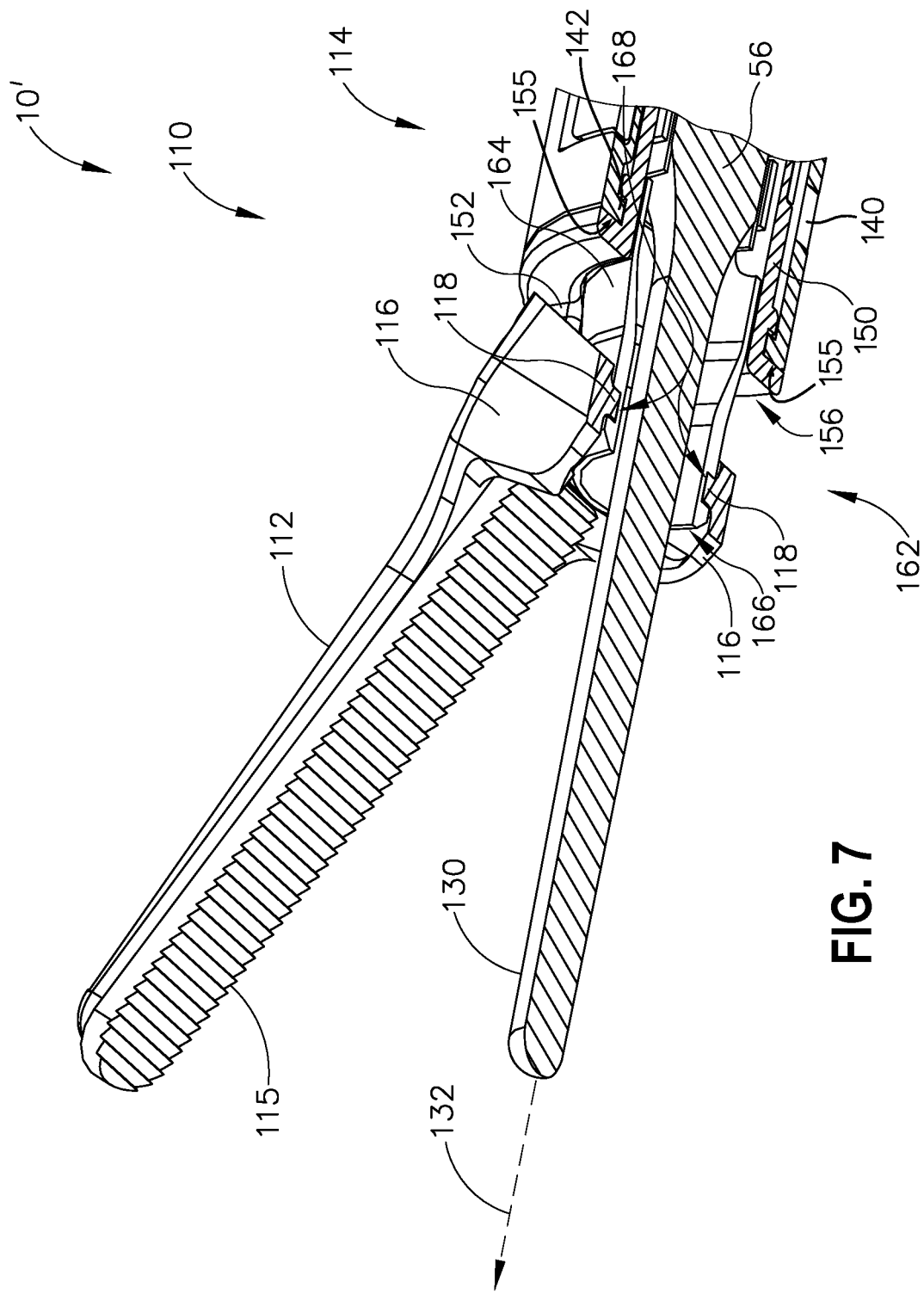
FIG. 7 depicts a sectional perspective view of a second example of an ultrasonic surgical instrument with a second end effector and a second distal shaft portion that may be readily incorporated into the ultrasonic surgical instrument of FIG. 1.
Figure 8:
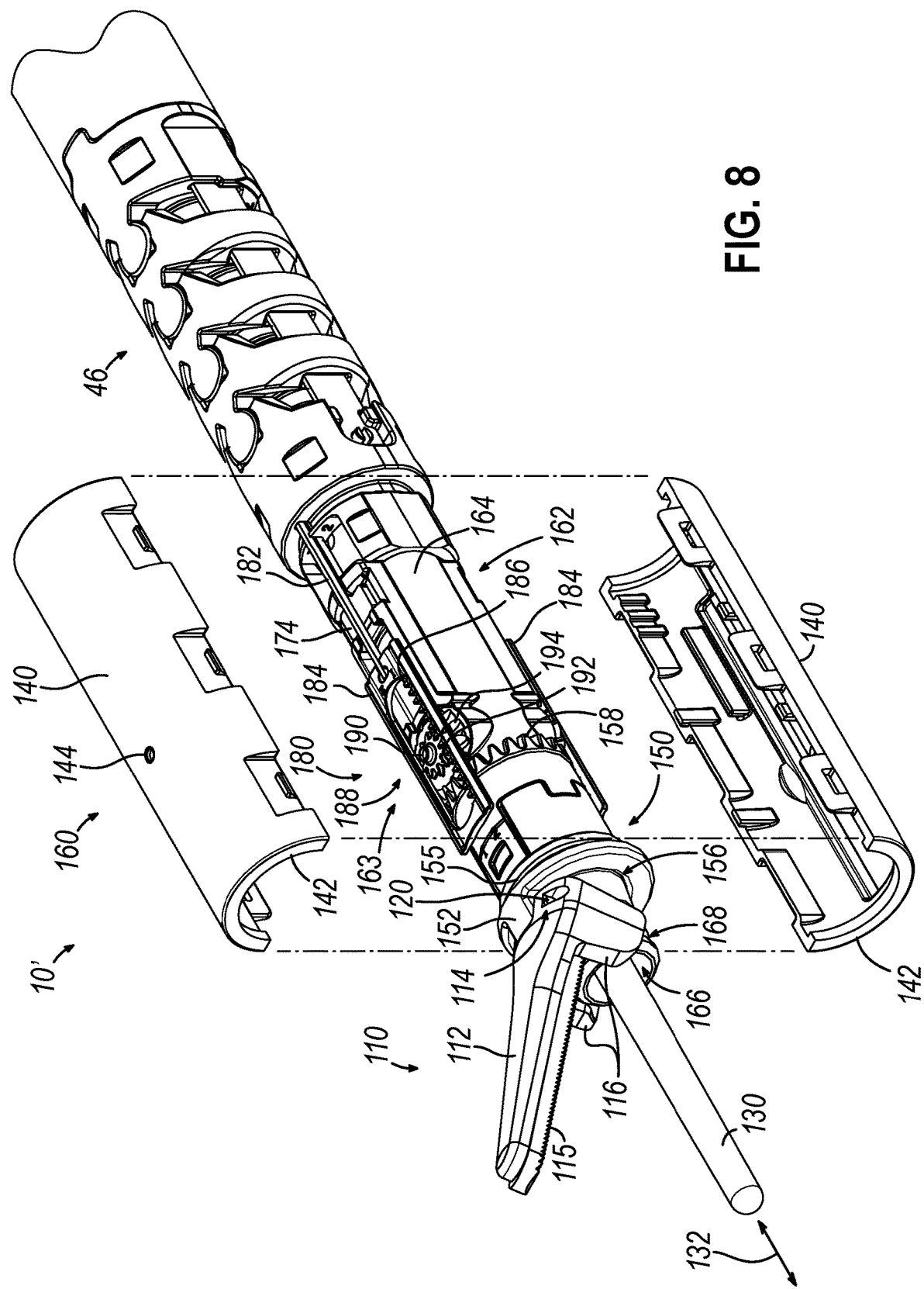
FIG. 8 depicts a partially exploded perspective view of the end effector and distal shaft portion of FIG. 7, showing a clamp arm closure assembly and an exemplary clamp arm clocking assembly having a first example of a rotation driver assembly.
Figure 9:
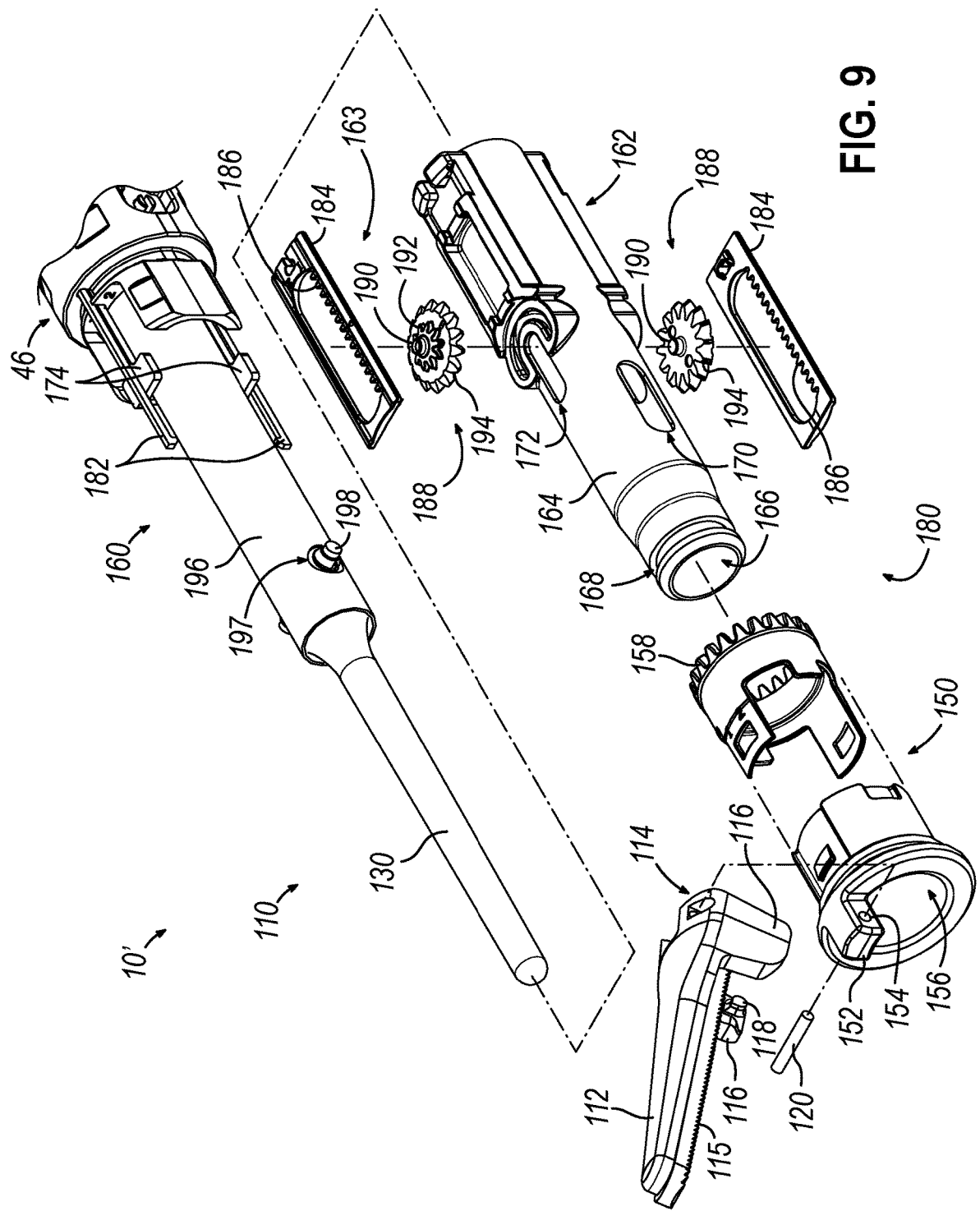
FIG. 9 depicts an exploded perspective view of the end effector and distal shaft portion of FIG. 7.

FIGS. 7-9 show a second example of an ultrasonic instrument (10') with a second end effector (110) and a second distal shaft portion (160) that may be readily incorporated into ultrasonic surgical instrument (10) (see FIG. 1) in replacement of end effector (16) and distal shaft portion (62) described above, respectively. As will be described in greater detail below, distal shaft portion (160) includes a clamp arm closure assembly (162) and an exemplary clamp arm clocking assembly (180) having a first example of a rotation driver assembly (163).

Clamp arm closure assembly (162) is configured to translate in order to drive clamp arm (112) of end effector (110) between an open position and closed position, regardless of the clocked position of clamp arm (112). In some instances, clamp arm closure assembly (162) is configured to (i) remain in a substantially fixed angular position about axis (132) relative to blade (130) as clamp arm (112) rotates into various clocked positions, and (ii) pivot clamp arm (112) toward and away from blade (130), regardless of the clocked position of clamp arm (112).

Additionally, as will be described in greater detail below, clamp arm closure assembly (162) and clamp arm clocking assembly (180) are configured to operate in accordance with the description herein regardless if end effector (110) is in a straight, non-articulated configuration (similar to that shown in FIG. 3B), or an articulated configuration (similar to that shown in FIGS. 4A-4B).

End effector (110) includes clamp arm (112), clamp pad (115), and ultrasonic blade (130); which are substantially similar to clamp arm (44), clamp pad (48), and ultrasonic blade (46) described above, respectively, with differences elaborated below. Therefore, ultrasonic blade (130) is positioned at a distal end of an acoustic drivetrain. This acoustic drivetrain includes transducer assembly (54) (see FIG. 5) and acoustic waveguide (56), which includes flexible portion (58) (see FIG. 3A).

Clamp arm (112) defines a pin hole (114) dimensioned to receive a pin (120) to pivotally couple clamp arm (112) with a rotating body (150) of clamp arm clocking assembly (180). As will be described in greater detail below, pin (120) pivotally couples clamp arm (112) with rotating body (150) of clamp arm clocking assembly (180) such that clamp arm (112) may pivot relative to rotating body (150), but also such that clamp arm (112) may rotate along with rotating body (150) about blade axis (132) relative to blade (130).

Clamp arm (112) also includes a pair of arms (116) that may be substantially similar to arms (51) described above, with differences elaborated below. Arms (116) include a respective inwardly presented protrusion (118) facing toward opposing arms (116). As best seen in FIG. 7, inwardly presented protrusions (118) are housed within an annular exterior channel (168) defined by a translating body (164) of clamp arm closure assembly (162). As will be described in greater detail below, actuation of translating body (164) along a path defined by axis (132) is configured to pivot clamp arm (112) between the open position and the closed position due to the interaction between inwardly presented protrusions (118) and annular exterior channel (168); while protrusions (118) are configured to actuate within channel (168) such that clamp arm (112) may rotate relative to translating body (164).

Distal shaft portion (160) includes a pair of outer casings (140) (see FIG. 8), a sleeve (196) (see FIG. 9), clamp arm closure assembly (162), and clamp arm clocking assembly (180). Outer casings (140) are configured to mate together in order to house various components of distal shaft portion (160). A proximal end of each casing (140) is fixed to a distal end of articulation section (64). Therefore, as articulation section (64) articulates in accordance with the description above, distal shaft portion (160) and end effector (110) also deflects.

Each outer casing (140) includes a distal circumferential rib (142) dimensioned to fit within an annular channel (155) of rotating body (150) (see FIG. 7). Interaction between circumferential ribs (142) and annular channel (155) allows rotating body (150) to rotate about axis (132) relative to outer casings (140), while also longitudinally constraining rotating body (150) relative to outer casings (140) along axis (132). In other words, ribs (142) and annular channel (155) allow rotting body (150) to rotate, yet remain substantially longitudinally fixed, relative to outer casings (140). As will be described in greater detail below, this interaction between rotating body (150) and outer casings (140) may allow clamp arm (112) to both pivot between the open and closed positions, as well as rotate into various clocked positions, relative to blade (130).

Each outer casing also defines a pin hole (144). As will be described in greater detail below, pin holes (144) are dimensioned to rotationally support a respective compound gear (188) of clamp arm clocking assembly (180).

Sleeve (196) houses waveguide (56) such that sleeve (196) is interposed between the outer diameter of waveguide (56) and the remaining portions of distal shaft portion (160). Additionally, sleeve (196) is coupled with waveguide (56) via waveguide pin (198) extending through a pin hole (197). Therefore, sleeve (196) is configured to move with the associated portion of waveguide (56) as waveguide (56) rotates and articulates in accordance with the description herein.

Clamp arm closure assembly (162) includes translating body (164) and a pair of translating drivers (174). Distal ends of translating drivers (174) are coupled to translating body (164) such that movement of drivers (174) causes corresponding movement of translating body (164). Translating drivers (174) extend proximally through articulation section (64) and shaft assembly (14) such that translating drivers (174) are operatively connected to at least one linear system actuator (36b, 36c, 36d, 36e, 36f) (see FIG. 6). Therefore, linear system actuator (36b, 36c, 36d, 36e, 36f) (see FIG. 6) coupled with the proximal end of translating drivers (174) may actuate translating drivers (174) proximally and distally relative to the rest of distal shaft portion (160).

The portion of translating drivers (174) extending through articulation section (64) are sufficiently flexible in order to bend along with articulation section (64) in accordance with the description herein. Additionally, the portion of translating drivers (174) extending through articulation section (64) is sufficiently rigid in order to communicate proximal and distal translation from the corresponding linear system actuator (36b, 36c, 36d, 36e, 360) to translating body (164), regardless of whether articulation section (64) is in a straight configuration or a bent configuration in accordance with the description herein. In other words, translating drivers (174) may actuate translating body (164) in accordance with the description herein, regardless of whether end effector (110) is in a straight, non-articulated, configuration, or an articulated configuration.

Figure 10:
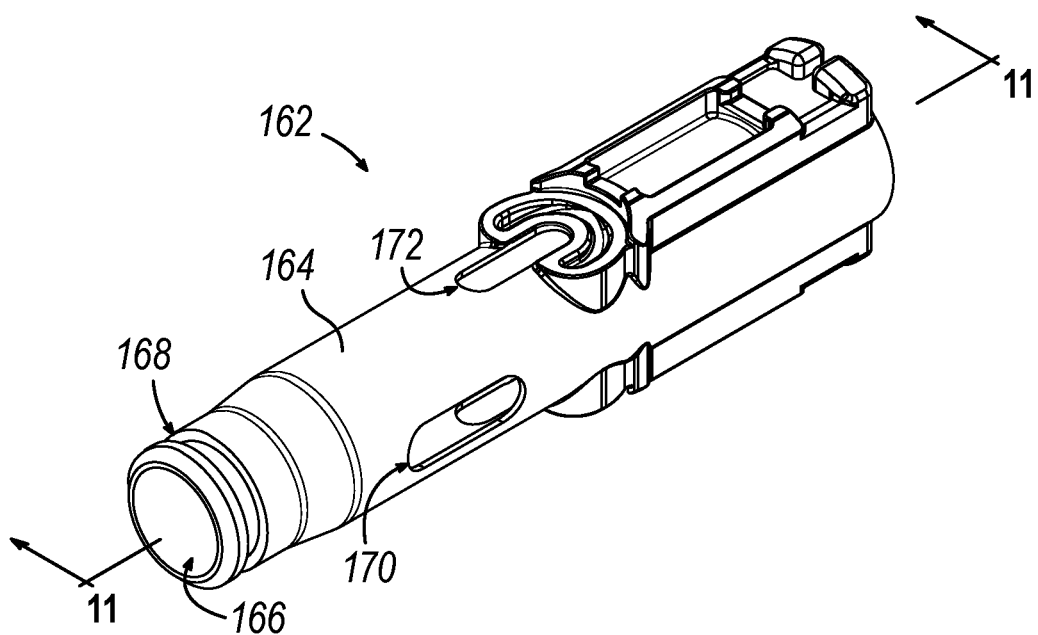
FIG. 10 depicts a perspective view of a translating body of the clamp arm closure assembly of FIG. 8.
Figure 11:
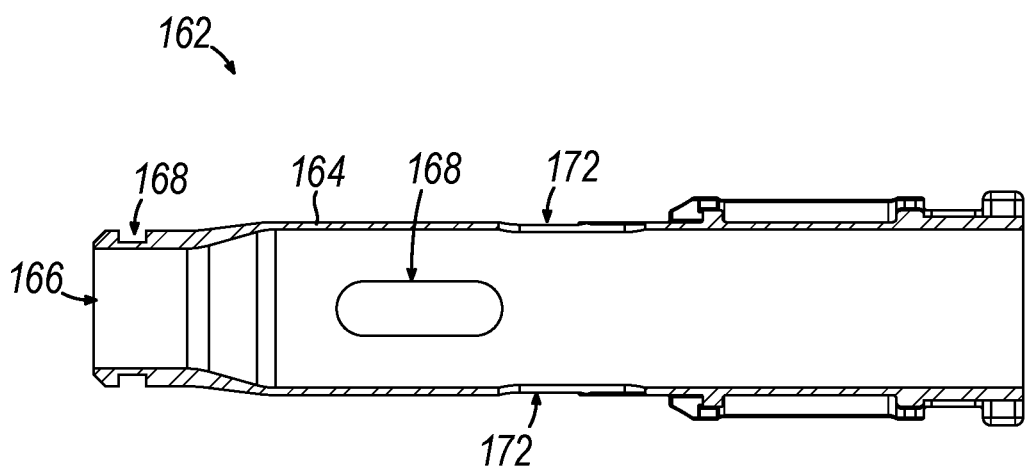
FIG. 11 depicts a cross-sectional view of the translating body of FIG. 10, taken along section line 11-11 of FIG. 10.
Figure 12:
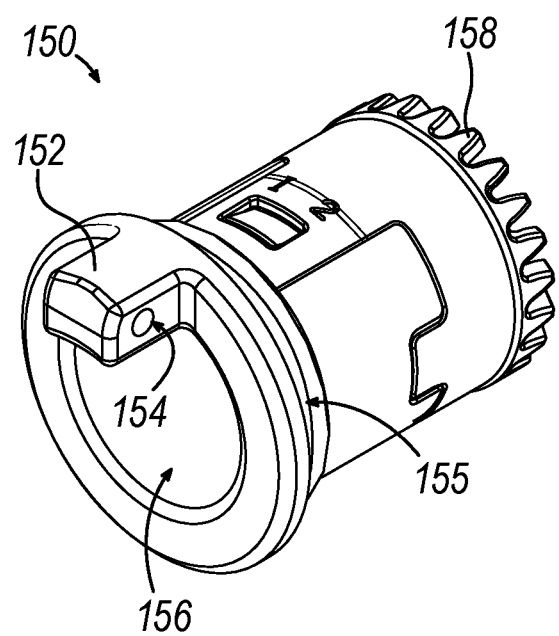
FIG. 12 depicts a perspective view of a rotating body of the clamp arm clocking assembly of FIG. 8.
Figure 13:
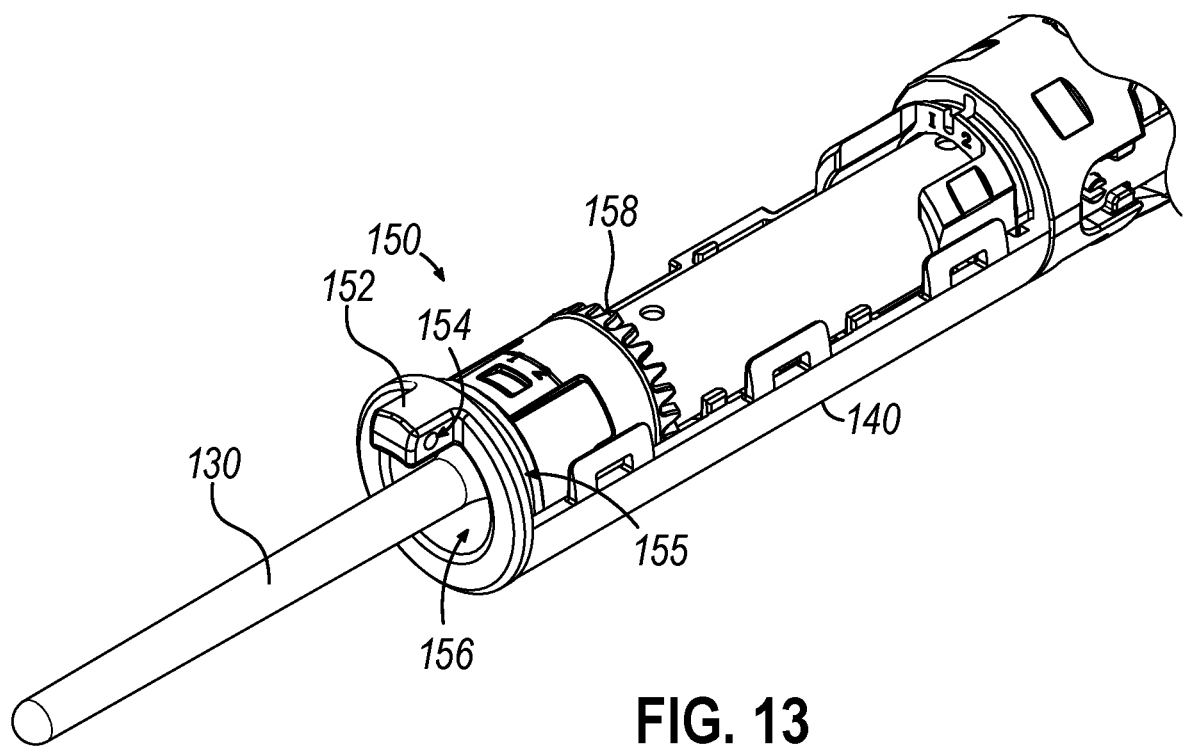
FIG. 13 depicts a perspective view of the rotating body of FIG. 12 disposed within a casing of the distal shaft portion of FIG. 7.
Figure 14:
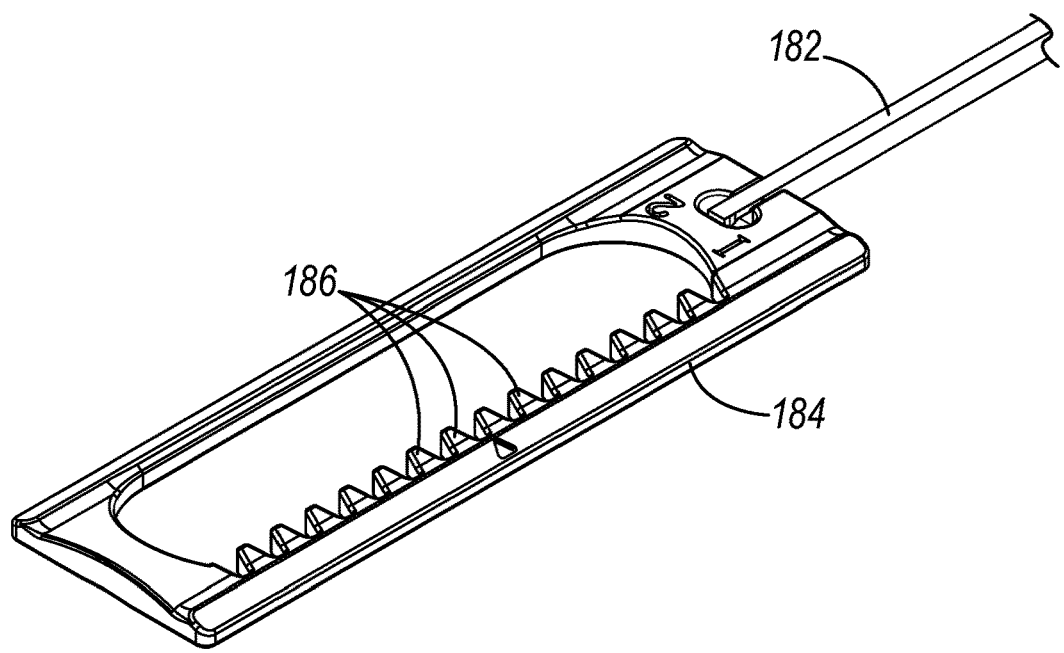
FIG. 14 depicts a perspective view of a rack of the rotation driver assembly of FIG. 8.
Figure 15:
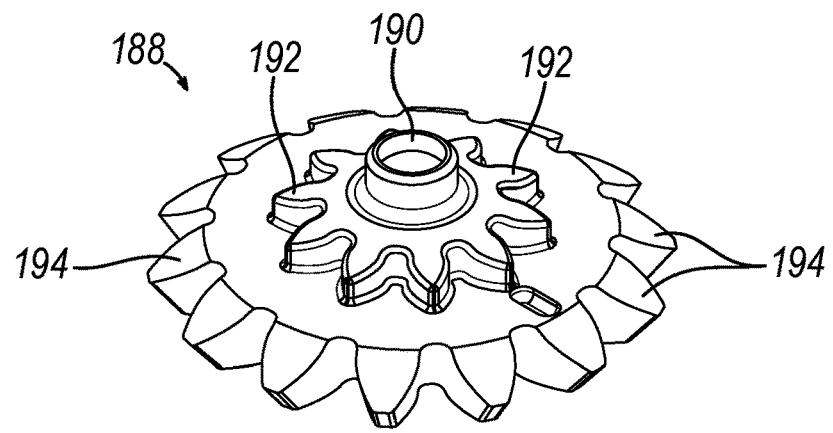
FIG. 15 depicts a perspective view of a compound gear of the rotation driver assembly of FIG. 8.
Figure 16:
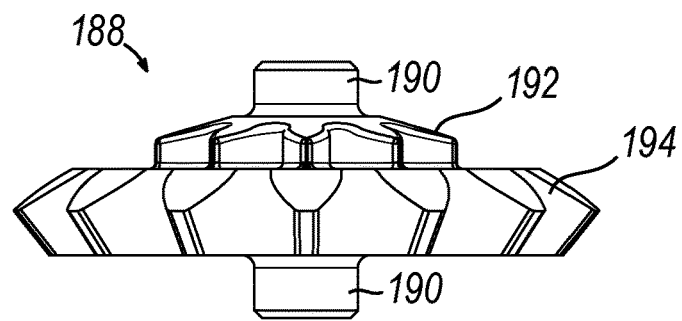
FIG. 16 depicts an elevational side view of the compound gear of FIG. 15.

As best shown in FIGS. 10-11, translating body (164) defines a hollow opening (166), annular exterior channel (168), a first pair of longitudinal slots (170) diametrically opposed with each other, and a second pair of longitudinal slots (172) diametrically opposed with each other. Hollow opening (166) extends from a proximal end to a distal end of translating body (164). Hollow opening (166) is dimensioned to slidably receive sleeve (196) such that translating body (164) may actuate relative to sleeve (196) and blade (130).

First pair of longitudinal slots (170) are dimensioned to house waveguide pin (198) such that translating body (164) may translate relative to sleeve (196) and blade (130), but such that translating body (164) is rotationally fixed relative to sleeve (196) and blade (130). In other words, as waveguide (56) and blade (130) are rotated in the direction indicated by arrow (66) (see FIG. 3A) in accordance with the description herein, waveguide pin (198) drives corresponding rotation of sleeve (196) and translating body (164). The length of longitudinal slots (170) may be long enough to accommodate translation of translating body (164) relative to waveguide pin (198) such that translating body (164) may pivot clamp arm (112) in accordance with the description herein without waveguide pin (198) inhibiting translation of body (164).

Second pair of longitudinal slots (172) are dimensioned to house a pin (190) of a respective compound gear (188) of clamp arm clocking assembly (180) such that translating body (164) may translate relative to compound gear (188), but such that compound gear (188) rotates with body (164) in response to waveguide pin (198) rotating body (164). The length of longitudinal slots (172) may be long enough to accommodate translation of translating body (164) relative to pins (190) of compound gears (188) such that translating body (164) may pivot clamp arm (112) in accordance with the depiction herein without pins (190) inhibiting translation of body (164).

Annular exterior channel (168) operatively houses inwardly presented protrusions (118) such that translation of body (164) drives clamp arm (112) to pivot about pin (120). Therefore, translating body (164) may be driven proximally and distally via translating drivers (174) in order to pivot clamp arm (112) about pin (120) toward and away from blade (130). Additionally, annular exterior channel (168) is configured to operatively house inwardly presented protrusions (118) as clamp arm (112) is clocked in various positions about axis (132) in accordance with the description herein. Therefore, annular exterior channel (168) acts as a track to retain inwardly presented protrusions (118). Because annular exterior channel (168) can operatively house inwardly presented protrusions (118) as clamp arm (112) is clocked in various positions relative to blade (130) about axis (132), translating body (164) may retain the ability to pivot clamp arm (112) in a plurality of clocked positions without having to rotate with clamp arm (112) about axis (132). Allowing translating body (164) to retain the ability to pivot clamp arm (112) in a plurality of clocked positions without having to rotate with clamp arm (112) about axis (132) may provide for a higher degree of precision for pivoting clamp arm (112) about pin (120).

In the current example, annular exterior channel (168) extends all the way around a circumferential portion of translating body (164) such that annular exterior channel (168) is continuous, however this is merely optional. Annular exterior channel (168) may extend circumferentially around only a portion of translating body (164) in order to accommodate the various intended clocking position of clamp arm (112). For instance, in some embodiments, annular exterior channel (168) may extend circumferentially around a portion of translating body (164) such that terminating ends of annular exterior channel (168) are 180 degrees apart.

As best seen in FIG. 9, clamp arm clocking assembly (180) includes rotating body (150), a pair of translating drivers (182), and rotation driver assembly (163) including a rack (184), which is associated with a respective translating driver (182), and a compound gear (188) associated with respective rack (184). Distal ends of translating drivers (182) are coupled to an associated rack (184) such that movement of drivers (182) causes corresponding movement of the associated rack (184). Rack (184) includes a linear array of teeth (186) that suitably mesh with teeth of a first gear (192) of compound gear (188). Therefore, translation of rack (184) results in rotation of compound gear (188).

Translating drivers (182) extend proximally through articulation section (64) and shaft assembly (14) such that translating drivers (182) are operatively connected to a respective linear system actuator (36b, 36c, 36d, 36e, 360 (see FIG. 6) other than linear system actuator (36b, 36c, 36d, 36e, 360 coupled to translating drivers (174). Therefore, linear system actuator (36b, 36c, 36d, 36e, 360 (see FIG. 6) coupled with the proximal end of translating drivers (182) may actuate translating drivers (182) proximally and distally relative to the rest of distal shaft portion (160) independently of translating drivers (174) and independently of each other. As will be described in greater detail below, translating drivers (182) are configured to actuate in opposing directions in order to drive rotation of rotating body (150).

The portion of translating drivers (182) extending through articulation section (64) are sufficiently flexible in order to bend along with articulation section (64) in accordance with the description herein. Additionally, the portion of translating drivers (182) extending through articulation section (64) is sufficiently rigid in order to communicate proximal and distal translation from the corresponding linear system actuator (36b, 36c, 36d, 36e, 360 to the associated rack (184), regardless of whether articulation section (64) is in a straight configuration or a bent configuration in accordance with the description herein. In other words, translating drivers (182) may actuate the associated rack (184) in accordance with the description herein, regardless of whether end effector (110) is in a straight, non-articulated, configuration, or an articulated configuration.

Rotating body (150) includes distally presented tongue (152) defining pin hole (154) and a gear including an annular array of proximally facing teeth (158). Rotating body (150) defines a hollow opening (156) extending from distally presented tongue (152) to proximally facing teeth (158). Hollow opening (156) is dimensioned to receive a portion of ultrasonic blade (130), a portion of waveguide (56), and translating body (164) of distal shaft portion (160).

Rotating body (150) defines annular channel (155) which houses circumferential ribs (142) of casing (140). Therefore, rotating body (150) is rotationally disposed within casings (140) in accordance with the description above. As shown in FIGS. 8-9, clamp arm (112) is pivotally coupled to rotating body (150) of clamp arm clocking assembly (180) at a distally presented tongue (152) of rotating body (150) via pin (120) and pin holes (114, 154). Therefore, clamp arm (112) may pivot about pin (120) relative to ultrasonic blade (130) between an open position and a closed position. Since rotating body (150) is also rotationally disposed within casings (140), as rotating body (150) rotates within casings (140) in accordance with the description herein, clamp arm (112) is rotated into various clocked positions. As will be described in greater detail below, proximally facing teeth (158) are configured to suitably mesh with both compound gears (188) such that compound gears (188) may drive rotation of rotating body (150) about axis (132) relative to blade (130) in order to rotate clamp arm (112) about axis (132) relative to blade (130).

Each compound gear (188) includes a pin (190), first gear (192), and a second gear (194). Pin (190) and gears (192, 194) may be of a unitary construction, separate pieces, or some combination of unitary construction of separate pieces. Pin (190) extends along an axis through first gear (192) and second gear (194). Each pin (190) is coupled with a pin hole (144) of a respective casing (140) such that suitable portions of compound gear (188) may rotate about the axis defined by pin (190) relative to casing (140) while inhibiting translation of compound gear (188) relative to casing (140). As mentioned above, pin (190) also extends through a longitudinal slot (172) defined by translating body (164); while longitudinal slot (172) is long enough to accommodate for translation of translating body (164), in accordance with the description herein, without unduly interfering with pin (190).

First gear (192) and second gear (194) of each compound gear (188) are configured to rotate about an axis defined by pin (190). First gear (192) and second gear (194) are coupled with each other such that as first gear (192) rotates an angular displacement about the axis defined by pin (190), second gear (194) also rotates the same angular displacement about the axis defined by pin (190). Second gear (194) has a larger diameter compared to first gear (192), such that teeth of second gear (194) travel a further distance compared to teeth of first gear (192), even though both gears (192, 194) are rotated about pin (190) with the same angular displacement. Gears (192, 194) and pin (190) may be coupled with each other through any suitable means as would be apparent to one skilled in the art in view of the teachings herein.

As mentioned above, first gear (192) of each compound gear (188) suitably meshes with teeth (186) of a respective rack (184) such that proximal and distal translation of the respective rack (184) rotates first gear (192) and second gear (194) about the axis defined by pin (190). As also mentioned above, rotating body (150) is rotatably disposed within casings (140) such that rotating body (150) may rotate about axis (132) defined by blade (130). Teeth of second gear (194) of each compound gear (188) suitably mesh with proximally facing teeth (158) of rotating body (150) such that rotation of each second gear (194) about the axis defined by respective pin (190) drives rotation of rotating body (150) about axis (132) defined by blade (130). It should be understood that since a first rack (184) and a respective first compound gear (188) are on diametrically opposite sides compared to a second rack (184) and a respective second compound gear (188), the first rack (184) and second rack (184) may travel in opposite directions in order for each compound gear (188) to drive rotation of rotating body (150) in the same angular direction. of rotating body (150) compared to proximal translation of one rack (184) and distal translation of the second rack (184).

Since clamp arm (112) is coupled to rotating body (150), translation of racks (184) in opposing directions is configured to rotate rotating body (150) and clamp arm (112) about axis (132) defined by blade (130) in either a first rotational direction and a second, opposite, rotational direction. In other words, opposing translation of translating drivers (182) is configured to change the clocked position of clamp arm (112) relative to blade (130).

Since second gear (194) is larger than first gear (192), compound gear (188) may provide mechanical advantage to clock rotating body (150) such that less force is required to be transmitted through translating drivers (182) as compared to use of gears with similar diameters. Additionally, the use of two racks (184) and two compound gears (188) may also reduce the force required to be transmitted through translating drivers (182) as compared to using just one rack (184) and one compound gear (188).

Rack (184) and compound gear (188) are configured to rotate with casings (140) and translating body (164) in accordance with the description herein. Therefore, when waveguide (56) rotates in the direction indicated by arrow (66) (see FIG. 3A), rack (184) and compound gear (188) also rotate in the direction indicated by arrow (66) (see FIG. 3A). Engagement between second gear (194) and proximally facing teeth (158) may drive rotating body (150) and clamp arm (112) to also rotate with waveguide (56) in the direction indicated by arrow (66) (see FIG. 3A). Therefore, when waveguide (56) is rotated in the direction indicated by arrow (66) (see FIG. 3A), clamp arm (112) may remain in the same clocked position relative to blade (130).

While in the current example, rack (184), compound gear (188), and proximally facing teeth (158) are used to convert translation of translating driver (182) into rotation of clamp arm (112) about blade (130), any other suitable means may be used to rotate clamp arm (112) about blade (130) as would be apparent to one skilled in the art in view of the teachings herein.

Figure 17:
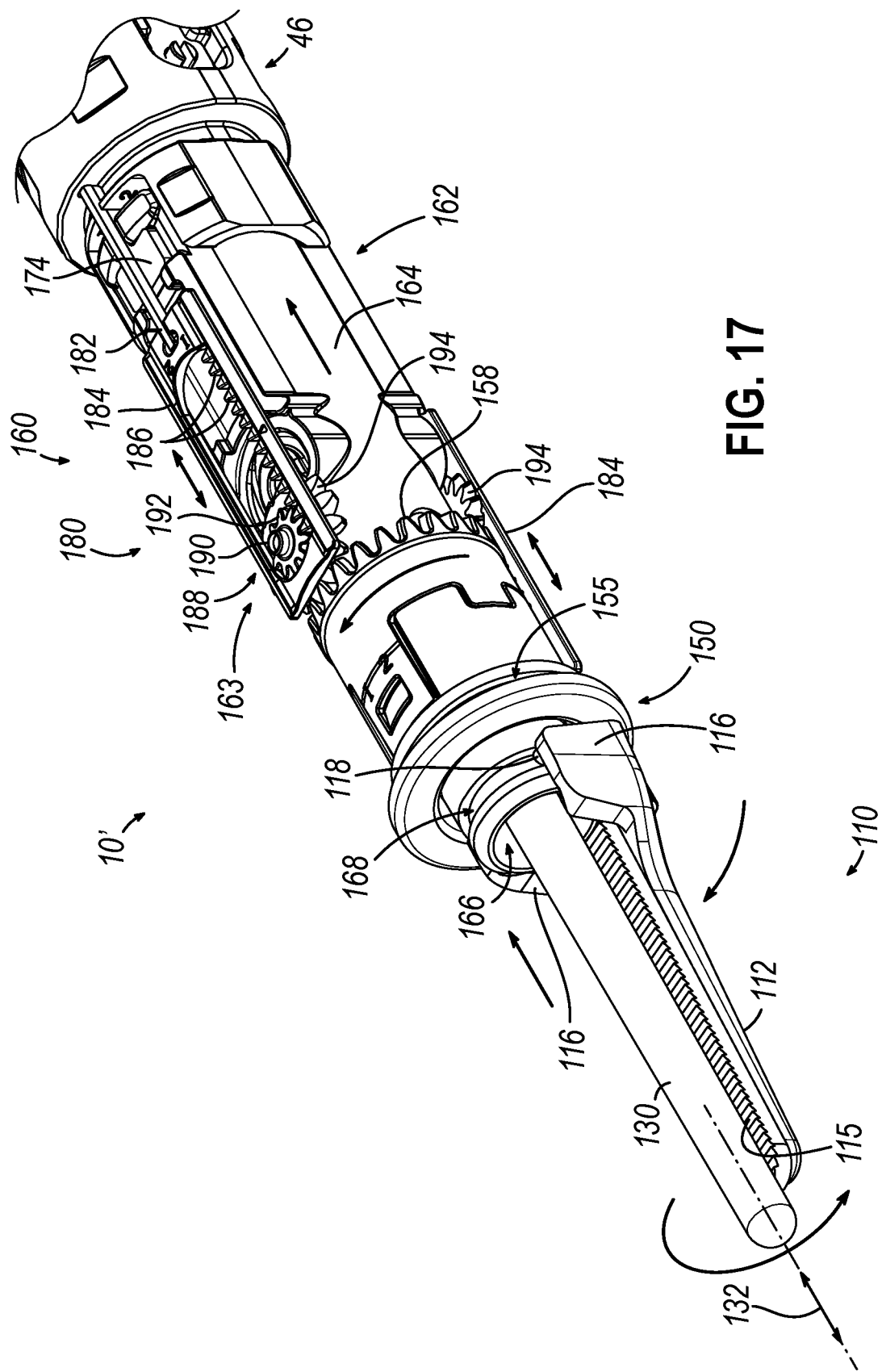
FIG. 17 depicts a perspective view of the end effector and distal shaft portion of FIG. 7, with certain portions omitted for clarity, where a clamp arm of the end effector of FIG. 7 is in a closed position in a clocked position.

In use, with respect to FIG. 17, clamp arm clocking assembly (180) and clamp arm closure assembly (162) are configured in the present example to rotate clamp arm (112) about blade (130), and then pivot clamp arm (112) about pin (120) in order to drive clamp arm (112) from the open position to the closed position. Clamp arm (112) may initially be in the open position and a first clocked position relative to blade (130). If the operator desires to change the clocked position of clamp arm (112), the operator may instruct instrument (10') to drive translating drivers (182) in opposing directions, which in turn rotates rotating body (150) and clamp arm (112) about blade (130) into a second clocked position.

It should be understood that as clamp arm (112) is rotated about blade (130) into the second clocked position, inwardly presented protrusions (118) are still operatively housed within annular exterior channel (168) of translating body (164). It should also be understood that translating body (164) remains in the same angular position about axis (132) of blade (130) as clamp arm (112) is rotated into the second clocked position. If the operator desires to rotate clamp arm (112) back toward the first clocked position, the operator may instruct instrument (10') to drive translating drivers (182) in opposing directions toward the initial position until clamp arm (112) is driven into the desired clocked position.

Next, with clamp arm (112) rotated about blade (130) into the desired clocked position, the operator may instruct instrument (10') to drive translating drivers (174) and translating body (164) proximally, which in turn pivots clamp arm (112) to the closed position. It should be understood that since inwardly presented protrusions (118) are operatively housed within annular exterior channel (168) while clamp arm (112) is in any clocked position, proximal translation of translating body (164) drives protrusions (118) proximally, which in turn pivots clamp arm (112) about pin (120) into the closed position. If the operator desires to pivot clamp arm (112) back toward the open position, the operator may instruct instrument (10') to drive translating drivers (174) distally until clamp arm (112) is pivoted about pin (120) into the desired position.

It should be understood that the operator may rotate clamp arm (112) to the second locked position while clamp arm (112) is in the closed position as well. In the current example, clamp arm (112) is rotated about blade (130) 180 degrees from the first clocked position. Clamp arm (112) may be rotated about blade (130) to any other suitably clocked position as would be apparent to one skilled in the art in view of the teachings herein. In the current example, rack (184) extends along a length to rotate clamp arm (112) a maximum of 180 degrees about blade (130) in either angular direction. It should be understood that rack (184) may have any suitable length to rotate clamp arm (112) about blade (130) at any suitable angular displacement as would be apparent to one skilled in the art in view of the teachings herein. For instance, rack (184) may have a suitable length to rotate clamp arm (112) 360 degrees, 270 degrees, 90 degrees, etc. about blade (130) in either angular direction.

III. Exemplary End Effector with Alternative Clamp Arm Clocking Assembly

Figure 18A:
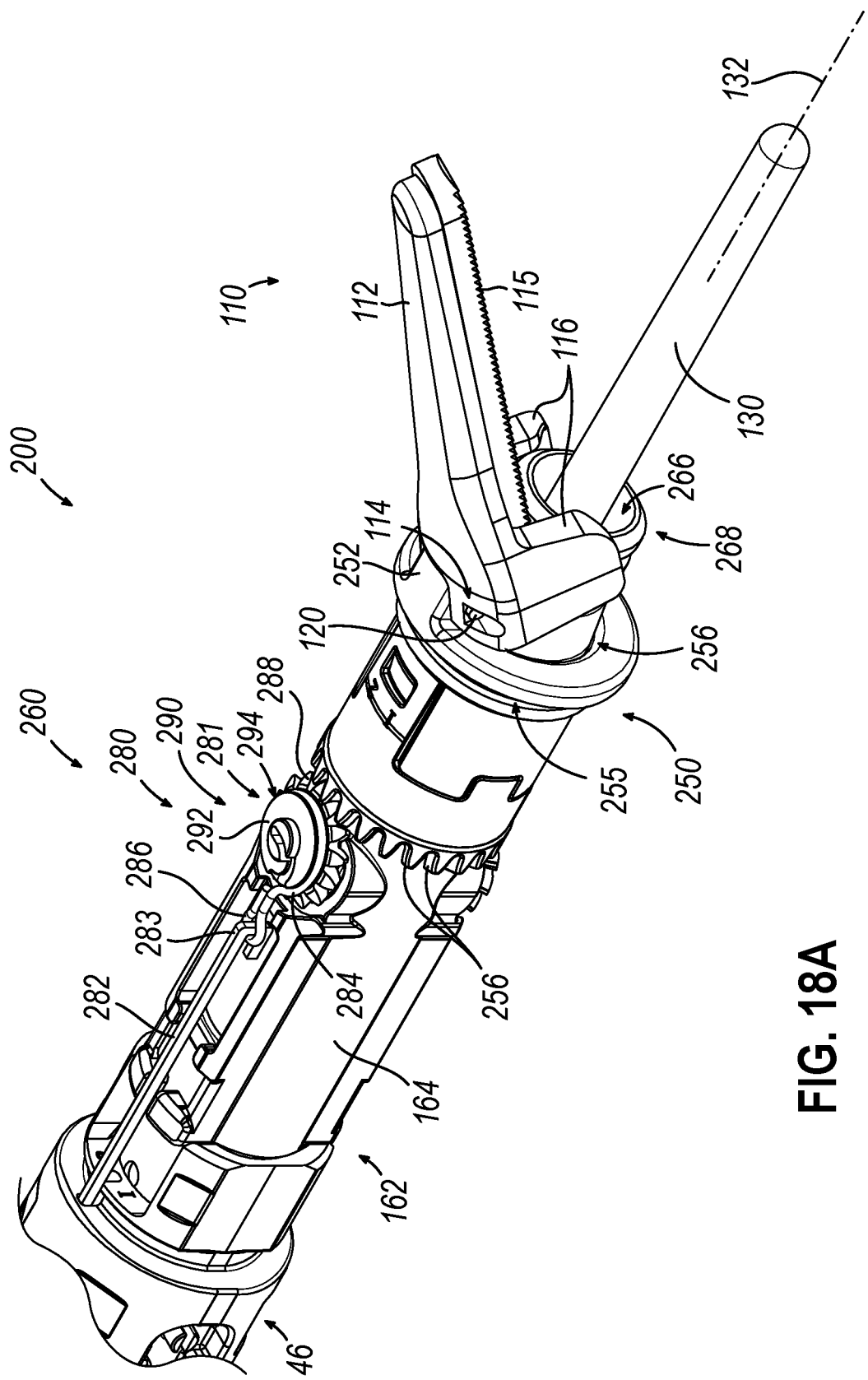
FIG. 18A depicts a perspective view of a third example of an ultrasonic surgical instrument including the end effector of FIG. 7 and a third distal shaft portion having a second example of a rotation driver assembly with a first exemplary pulley and gear assembly, with certain portions omitted for clarity, where a clamp arm of the end effector is in an open position in a first clocked position.
Figure 18B:
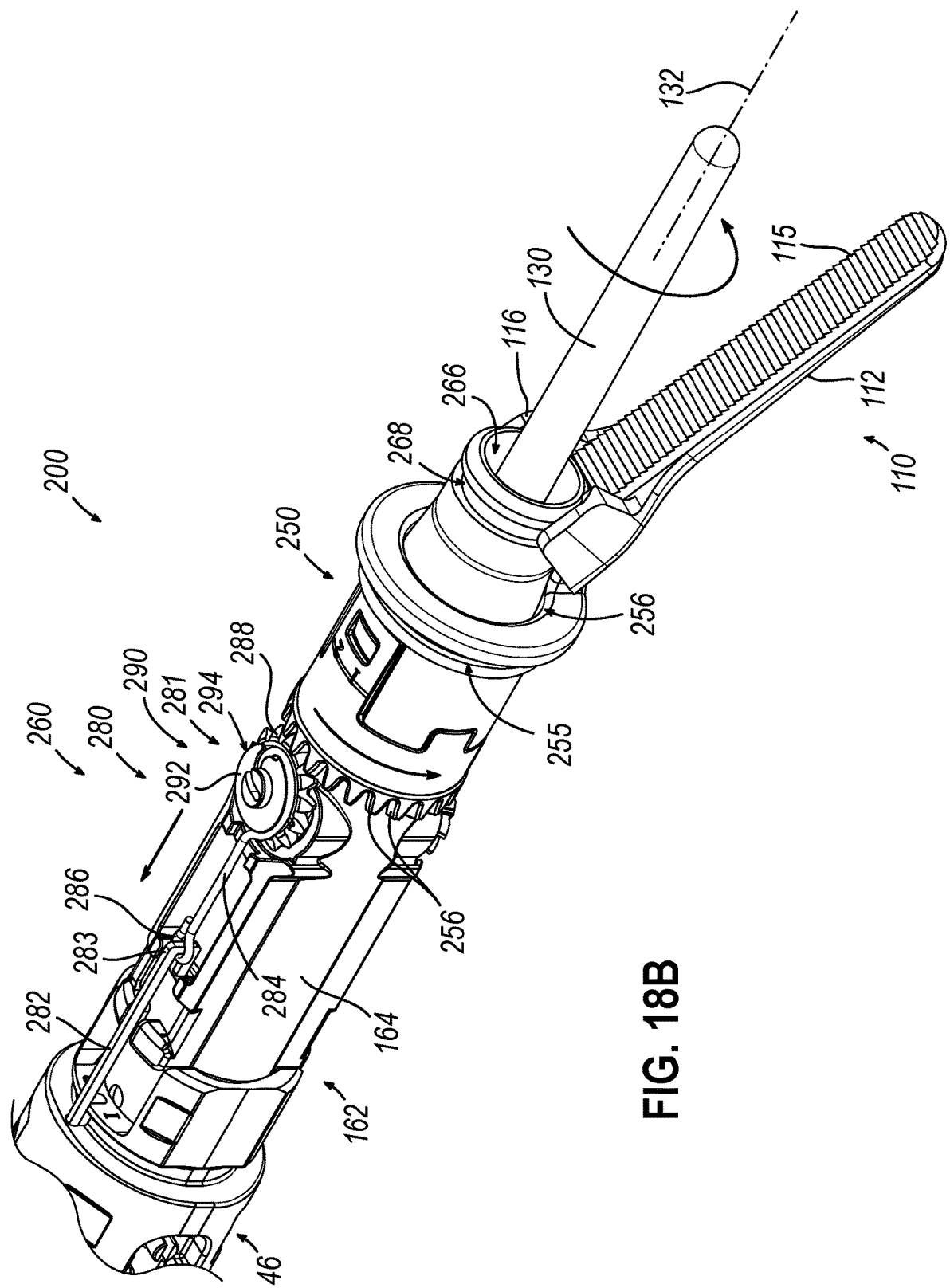
FIG. 18B depicts a perspective view of the end effector and distal shaft portion of FIG. 18A, with certain portions omitted for clarity, where the clamp arm of FIG. 18A is in the open position in a second clocked position.
Figure 19:
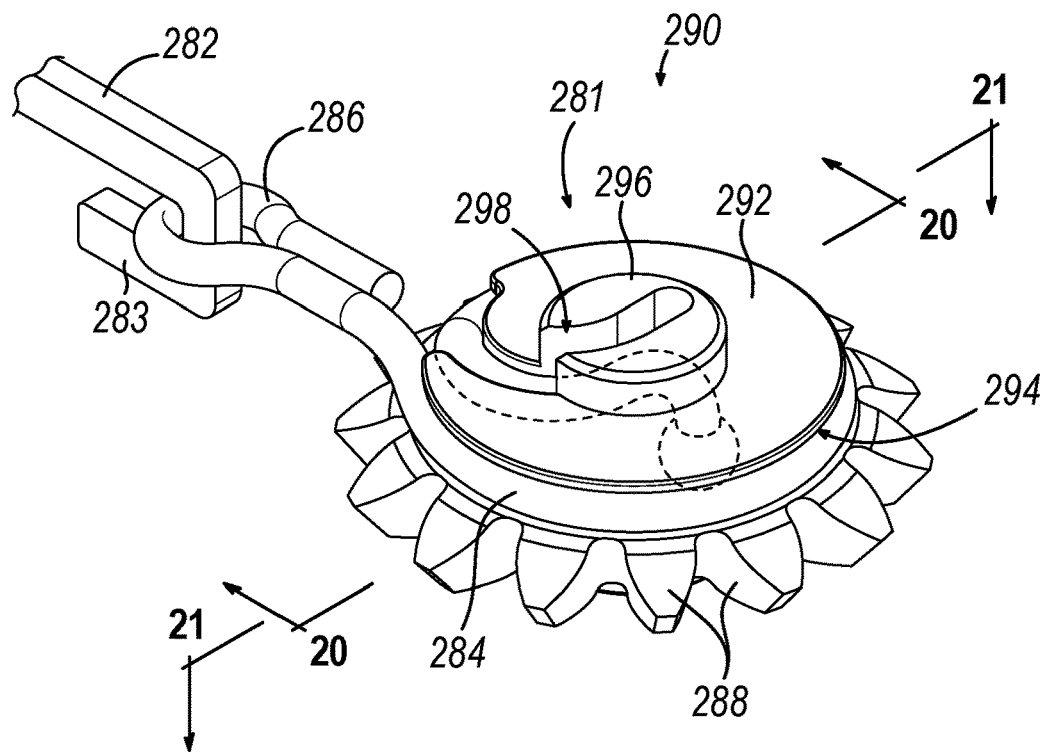
FIG. 19 depicts a perspective view of a translating driver, a cable, and a pulley and gear assembly of the distal shaft portion of FIG. 18A.
Figure 20:
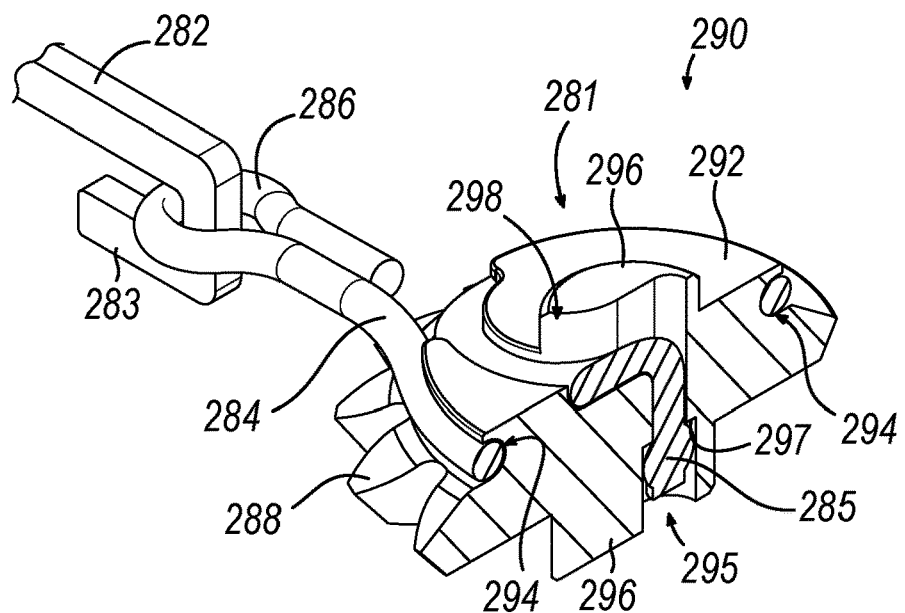
FIG. 20 depicts a sectional perspective view of the translating driver, the cable, and the pulley and gear assembly of FIG. 19, taken along section line 20-20 of FIG. 19.
Figure 21:
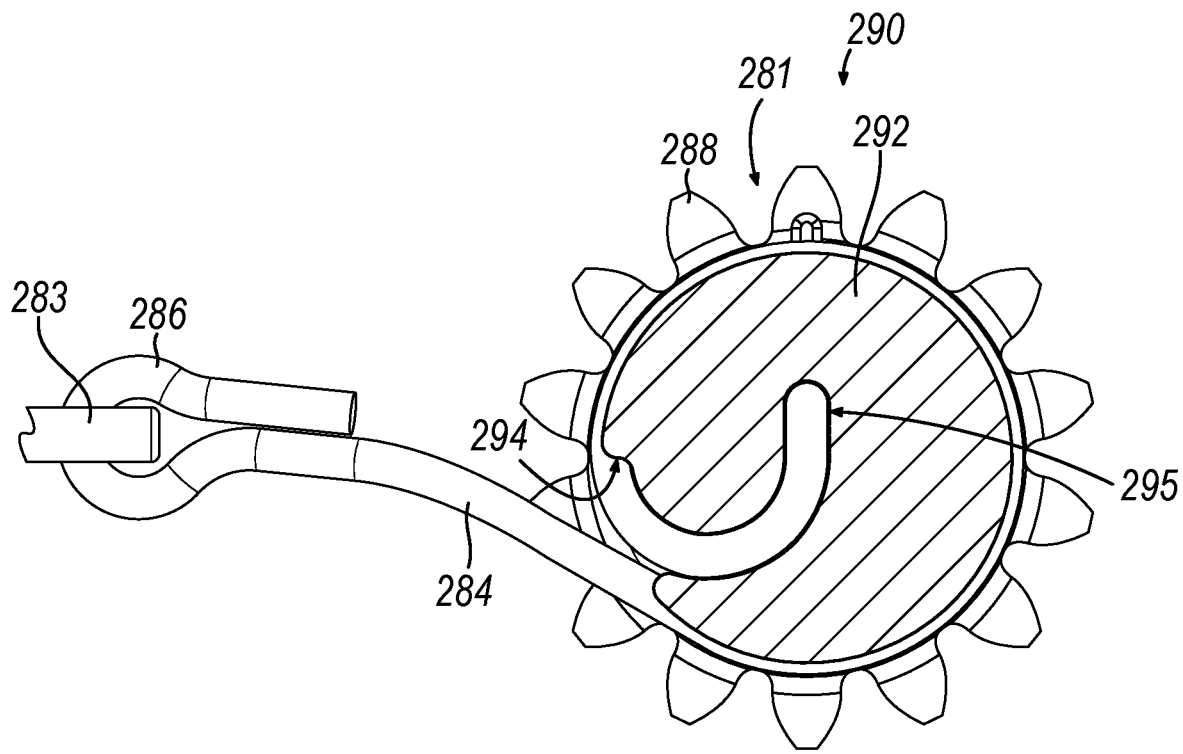
FIG. 21 depicts a cross-sectional view of the translating driver, the cable, and the pulley and gear assembly of FIG. 19, taken along section line 21-21 of FIG. 19.

FIGS. 18A-18B show a third example of an ultrasonic instrument (200) with end effector (110) and a third distal shaft portion (260) that may be readily incorporated into ultrasonic surgical instrument (10) (see FIG. 1) in replacement of end effector (16) and distal shaft portion (62) described above, respectively. Ultrasonic instrument (200) is substantially similar to instrument (10') described above, with differences elaborated below. Therefore, distal shaft portion (260) is substantially similar to distal shaft portion (160) described above, with differences elaborated below.

To this end, distal shaft portion (260) includes clamp arm closure assembly (162) and an alternative clamp arm clocking assembly (280). Similar to clamp arm clocking assembly (180) described above, clamp arm clocking assembly (280) is configured to drive clamp arm (112) of end effector (110) into various clocked positions around an ultrasonic blade (130) of end effector (110). However, instead of a rack (184) and compound gear (188) of rotation driver assembly (163) being used to convert translational movement of translating drivers (282) into rotational movement of clamp arm (112), clamp arm clocking assembly (280) includes a second example of a rotation driver assembly (281) with a cable (284) and a first exemplary pulley and gear assembly (290) configured to convert translational movement of translating drivers (282) into rotational movement of clamp arm (112).

Clamp arm clocking assembly (280) includes a rotating body (250), a pair of translating drivers (282), and rotation driver assembly (281), which includes cable (284) associated with a respective translating driver (282) and pulley and gear assembly (290) associated with a respective cable (284). Distal ends of translating drivers (282) include a hook (283) that receives a proximal loop (286) of cable (284) such that proximal movement of translating drivers (282) pulls the respective cable (284) proximally. As will be described in greater detail below, cable (284) wraps around a pulley body (292) of pulley and gear assembly (290) with sufficient tension such that proximal translation of cable (284) rotates pulley body (292) and the rest of pulley and gear assembly (290).

Translating drivers (282) extend proximally through articulation section (64) such that translating drivers (282) are operatively connected to a respective linear system actuator (36b, 36c, 36d, 36e, 360 (see FIG. 6) other than linear system actuator (36b, 36c, 36d, 36e, 360 coupled to translating drivers (174). Therefore, linear system actuator (36b, 36c, 36d, 36e, 360 (see FIG. 6) coupled with the proximal end of translating drivers (282) may actuate translating drivers (282) proximally and distally relative to the rest of distal shaft portion (260) independently of translating drivers (174) and independently of each other. As will be described in greater detail below, translating drives (282) are configured to actuate in opposing directions in order to drive rotation of rotating body (250).

The portion of translating drivers (282) extending through articulation section (64) are sufficiently flexible in order to bend along with articulation section (64) in accordance with the description herein. Additionally, the portion of translating drivers (282) extending through articulation section (64) is sufficiently rigid in order to communicate proximal and distal translation from the corresponding linear system actuator (36b, 36c, 36d, 36e, 360 to distal hook (283), regardless of whether articulation section (64) is in a straight configuration or a bent configuration in accordance with the description herein. In other words, translating drivers (282) may actuate in accordance with the description herein, regardless of whether end effector (110) is in a straight, non-articulated, configuration, or an articulated configuration.

Rotating body (250) may be substantially similar to rotating body (150) described above. Therefore, rotating body (250) includes distally presented tongue (252) defining a pin hole (not shown), and a gear including an annular array of proximally facing teeth (258). Rotating body (250) defines a hollow opening (256) extending from distally presented tongue (252) to proximally facing teeth (258). Hollow opening (256) is dimensioned to receive a portion of ultrasonic blade (130), a portion of waveguide (56), and translating body (164) of distal shaft portion (260).

Rotating body (250) defines annular channel (255) which houses circumferential ribs (142) of casing (140). Therefore, rotating body (250) is rotationally disposed within casings (140) in accordance with the description above. Clamp arm (112) is pivotally coupled to rotating body (250) of clamp arm clocking assembly (280) at distally presented tongue (252) of rotating body (250) via pin (120) and pin holes (114). Therefore, clamp arm (112) may pivot about pin (120) relative to ultrasonic blade (130) between an open position and a closed position in accordance with the description herein. Since rotating body (250) is also rotationally disposed within casings (140), as rotating body (250) rotates within casings (140) in accordance with the description herein, clamp arm (112) is rotated into various clocked positions. As will be described in greater detail below, proximally facing teeth (258) are configured to suitably mesh with gears (288) from both pulley and gear assemblies (290) such that gears (288) may drive rotation of rotating body (250) about axis (132) relative to blade (130) in order to rotate clamp arm (112) about axis (132) relative to blade (130).

Similar to compound gears (188) described above, pulley and gear assemblies (290) are rotationally coupled to a respective casing (140) and are located on diametric ends of translating body (164). Each pulley and gear assembly (290) includes a central projection (296). Similar to pin (190) of compound gear (188), central projection (296) is disposed within pin hole (144) of a respective casing (140) and second longitudinal slot (172) of translating body (164). Therefore, pulley and gear assemblies (290) may rotate relative to casings (140) and translating body (164) about the axis defined by central projection (296).

Pulley and gear assemblies (290) each include pulley body (292) and gear (288). Pulley body (292) and gear (288)

are configured to rotate together about an axis defined by central projection (296). Projection (296), pulley body (292), and gear (288) may be formed unitarily, with separate pieces, or a combination thereof.

Pulley body (292) defines a cable recess (294) and a central coupling channel (298) extending between a lower opening (295) and cable recess (294). Cable (284) wraps around cable recess (294) of pulley body (292) with sufficient tension such that proximal translation of cable (284) rotates pulley body (292) and the rest of pulley and gear assembly (290). Central coupling channel (298) extends between lower opening (295) defined by central projection (296) and cable recess (294) to couple cable (284) with pulley and gear assembly (290). In particular, cable (284) includes a distal ball (285) configured to abut against a ledge (297) of lower opening (295) to prevent a distal end of cable (284) from being pulled through lower opening (295), thereby preventing cable (284) from accidentally disassociating with pulley and gear assembly (290).

During coupling, a proximal end of cable (284) may be inserted through lower opening (295) and central coupling channel (298). After the proximal end of cable (284) is inserted past central coupling channel (298), a portion of cable (284) may be wrapped around cable recess (294) until distal ball (285) abuts against ledge (297) and cable (284) rests against cable recess (294) with sufficient tension. Next, the proximal end of cable (284) may be wrapped around hook (293) and then the user may form loop (286). Of course, the user may also form loop (286) and then wrap loop (286) around hook (283). Loop (286) may be formed by any suitable means as would be apparent to one skilled in the art in view of the teachings herein. Additionally, cable (284) and translating driver (282) may be coupled using any other suitable means as would be apparent to one skilled in the art in view of the teachings herein, such that loop (286) and hook (283) are optional.

As mentioned above, rotating body (250) is rotationally disposed within casings (140) such that rotating body (250) may rotate about axis (132) defined by blade (130). Teeth of gear (288) of each pulley and gear assembly (290) suitably mesh with proximally facing teeth (258) of rotating body (250) such that rotation of each gear (288) about the axis defined by central projection (296) drives rotation of rotating body (250) about axis (132) defined by blade (130). It should be understood that since a first cable (284) and a respective first pulley and gear assembly (290) are on diametrically opposite sides of translating body (164) compared to a second cable (284) and a respective second pulley and gear assembly (290), the first cable (284) and second cable (284) may travel in opposite directions such that as one cable (284) unwraps around its respective pulley body (292), the other cable (284) is wrapped around its respective pulley body (292).

With clamp arm (112) coupled to rotating body (250), translation of cables (284) in opposing directions is configured to rotate pulley and gear assembly (290), which in turn rotates rotating body (250) and clamp arm (112) about axis (132) defined by blade (130) in either a first rotational direction and a second, opposite, rotational direction. In other words, as exemplified between FIGS. 18A-18B, opposing translation of translating drivers (182) is configured to change the clocked position of clamp arm (112) relative to blade (130). During exemplary use, the operator may clock clamp arm (112) into any suitable clocked position relative to blade (130) as would be apparent to one skilled in the art in view of the teachings herein.

Cable (284) and pulley and gear assembly (290) are configured to rotate with casings (140) and translating body (164) in accordance with the description herein. Therefore, when waveguide (56) rotates in the direction indicated by arrow (66) (see FIG. 3A), cable (284) and pulley and gear assembly (290) also rotate in the direction indicated by arrow (66) (see FIG. 3A). Engagement between gear (288) and proximally facing teeth (158) may drive rotating body (250) and clamp arm (112) to also rotate with waveguide (56) in the direction indicated by arrow (66) (see FIG. 3A). Therefore, when waveguide (56) is rotated in the direction indicated by arrow (66) (see FIG. 3A), clamp arm (112) may remain in the same clocked position relative to blade (130).

Figure 22:
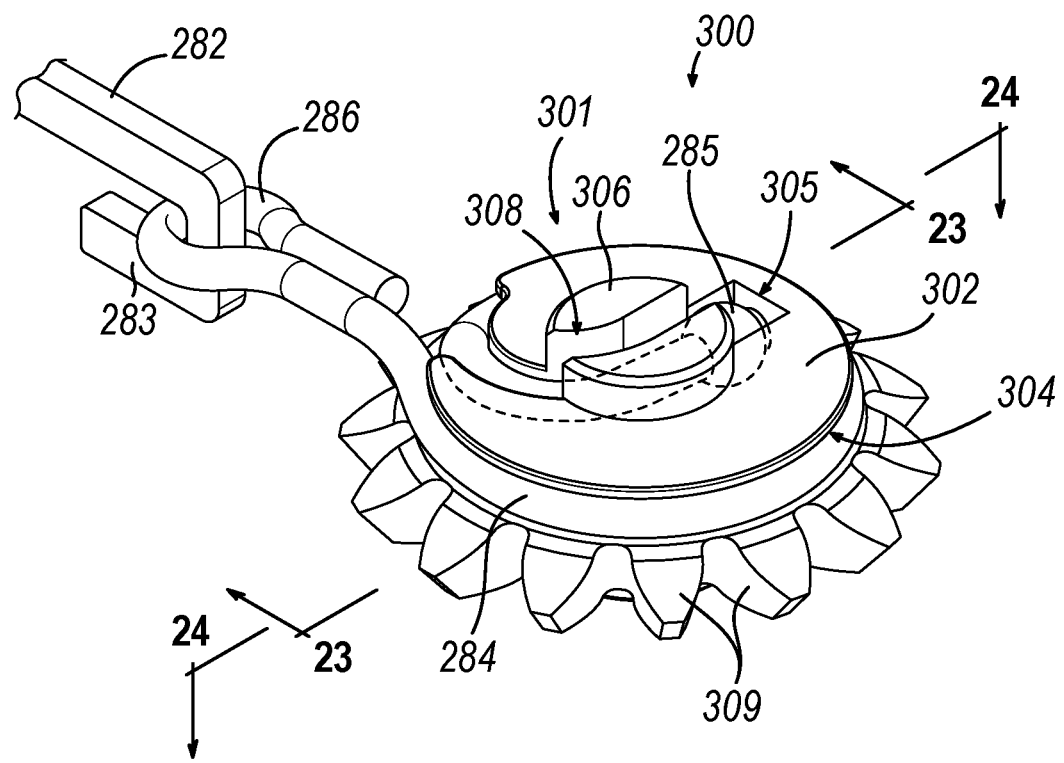
FIG. 22 depicts a perspective view of a third example of a rotation driver assembly with a second exemplary pulley and gear assembly that may be readily incorporated into the distal shaft portion of FIG. 18A.
Figure 23:
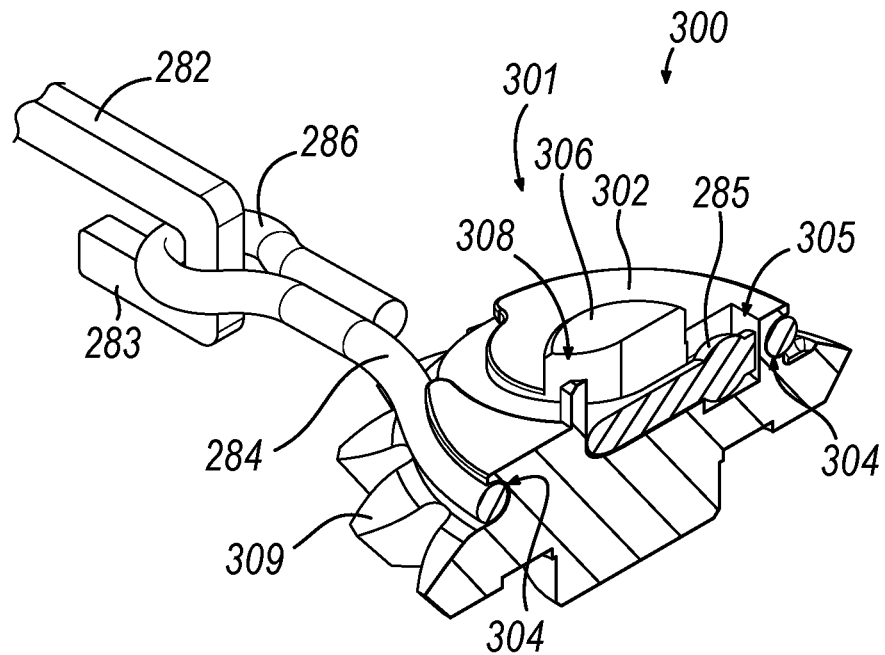
FIG. 23 depicts a sectional perspective view of the pulley and gear assembly of FIG. 22, taken along section line 23-23 of FIG. 22.
Figure 24:
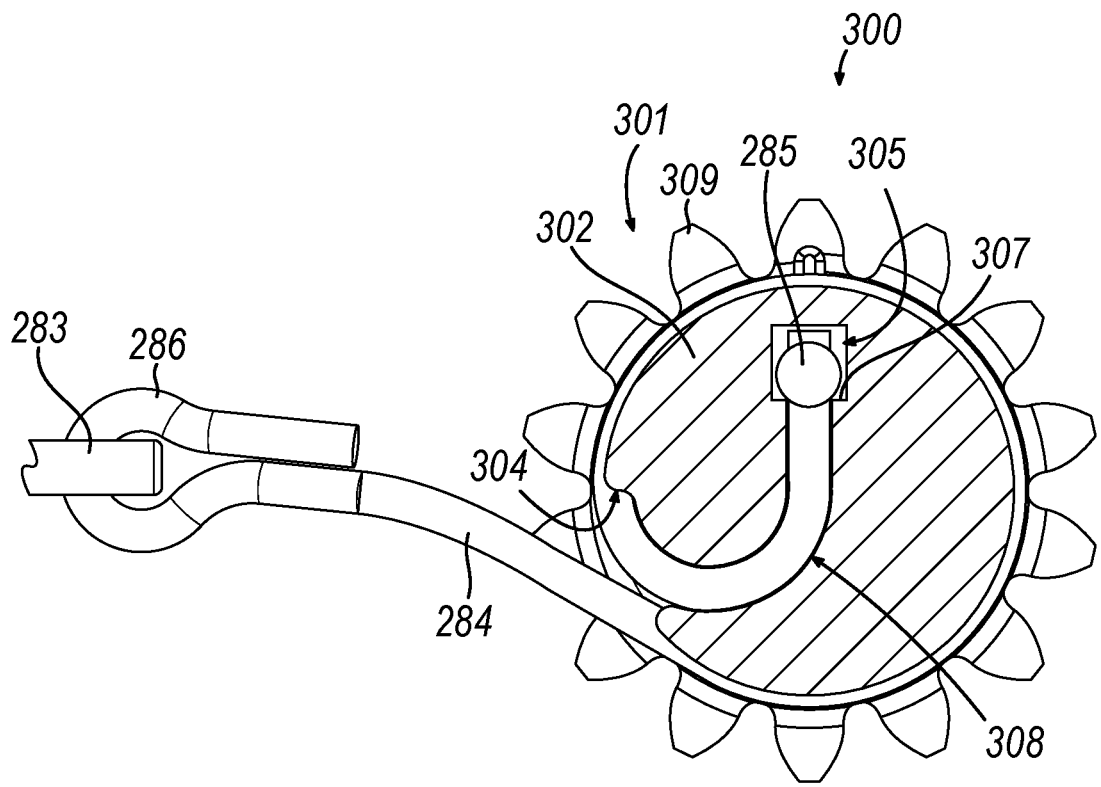
FIG. 24 depicts a cross-sectional view of the pulley and gear assembly of FIG. 22, taken along section line 24-24 of FIG. 22.

FIGS. 22-24 show a third example of a rotation driver assembly (301) including a second exemplary pulley and gear assembly (300) that may be readily incorporated into clamp arm clocking assembly (280) in replacement of pulley and gear assembly (290) described above. Pulley and gear assembly (300) is substantially similar to pulley and gear assembly (290) described above, except pulley and gear assembly (300) couples with cable (284) in a different fashion.

Pulley and gear assembly (300) includes a pulley body (302), a central projection (306), and a gear (309); which may be substantially similar to pulley body (292), central projection (296), and gear (288) described above, respectively, with differences described below. Therefore, gear (309) is configured to suitably mesh with rotating body (250), while projection (306) is configured to be rotationally disposed within pin hole (144) of a respective casing (140) and second longitudinal slot (172) of translating body (164).

Pulley body (302) defines a cable recess (304) substantially similar to cable recess (294) described above. Pulley body (302) also defines a central coupling channel (308) extending between cable recess (304) and a top opening (305). In the current example, central coupling channel (308) extends through central projection (306). However, this is optional, as central coupling channel (308) may extend on pulley body (302) around central projection (306).

Rather than defining a lower opening (295), like pulley body (292) described above, pulley body (302) defines a top opening (305) dimensioned to receive distal ball (285) to couple with cable (284). Top opening (305) does not extend through pulley body (292). Therefore, instead of inserting a proximal end of cable (284) through lower opening (295), a user may simply insert ball (285) into top opening (305) such that ball (285) abuts against ledge (307), and then wrap cable (284) around cable recess (304) in accordance with the description herein. In other words, the user may couple cable (284) with pulley and gear assembly (300) without threading the proximal end of cable (284) through pulley and gear assembly (300). Therefore, the user may more easily attach cable (284) to pulley and gear assembly (300) after pulley and gear assembly (300) is attached to other components of instrument (200), such as translating body (164).

Figure 25:
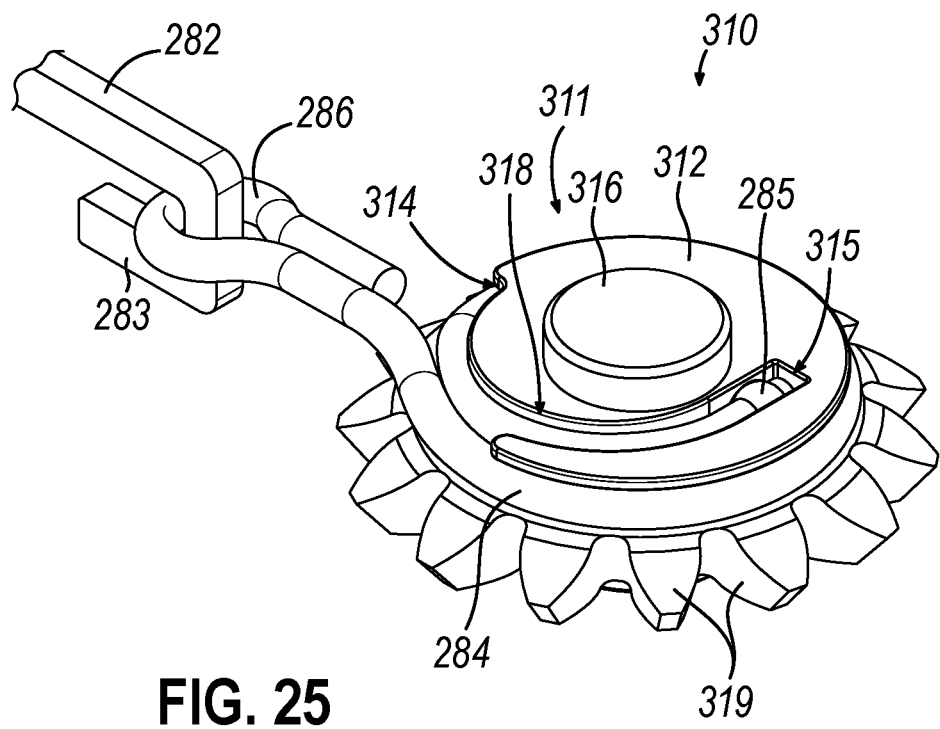
FIG. 25 depicts a perspective view of a fourth example of a rotation driver assembly with a third exemplary pulley and gear assembly that may be readily incorporated into the distal shaft portion of FIG. 18A.

FIG. 25 shows a fourth example of a rotation driver assembly (311) including a third exemplary pulley and gear assembly (310) that may be readily incorporated into clamp arm clocking assembly (280) in replacement of pulley and gear assembly (290) described above. Pulley and gear assembly (310) is substantially similar to pulley and gear assembly (300) described above, except coupling channel (318) and top opening (315) do not extend through central projection (316).

Pulley and gear assembly (310) includes a pulley body (312), a central projection (316), and a gear (319); which may be substantially similar to pulley body (302), central projection (306), and gear (309) described above, respectively, with differences described below.

Pulley body (312) defines a cable recess (314) substantially similar to cable recess (304) described above. Pulley body (312) also defines coupling channel (318) extending between cable recess (314) and a top opening (315). In the current example coupling channel (318) extends on pulley body (312) around central projection (316), rather than though central projection (316). Therefore, the routing of coupling channel (318) may avoid disruption of the axle bearing surfaces of central projection (316).

Similar to top opening (305) described above, a user may simply insert ball (285) into top opening (315) such that ball (285) abuts against ledge, and then wrap cable (284) around cable recess (314) in accordance with the description herein. In other words, the user may couple cable (284) with pulley and gear assembly (310) without threading the proximal end of cable (284) through pulley and gear assembly (310). Therefore, the user may more easily attach cable (284) to pulley and gear assembly (310) after pulley and gear assembly (310) is attached to other components of instrument (200), such as translating body (164).

Figure 26:
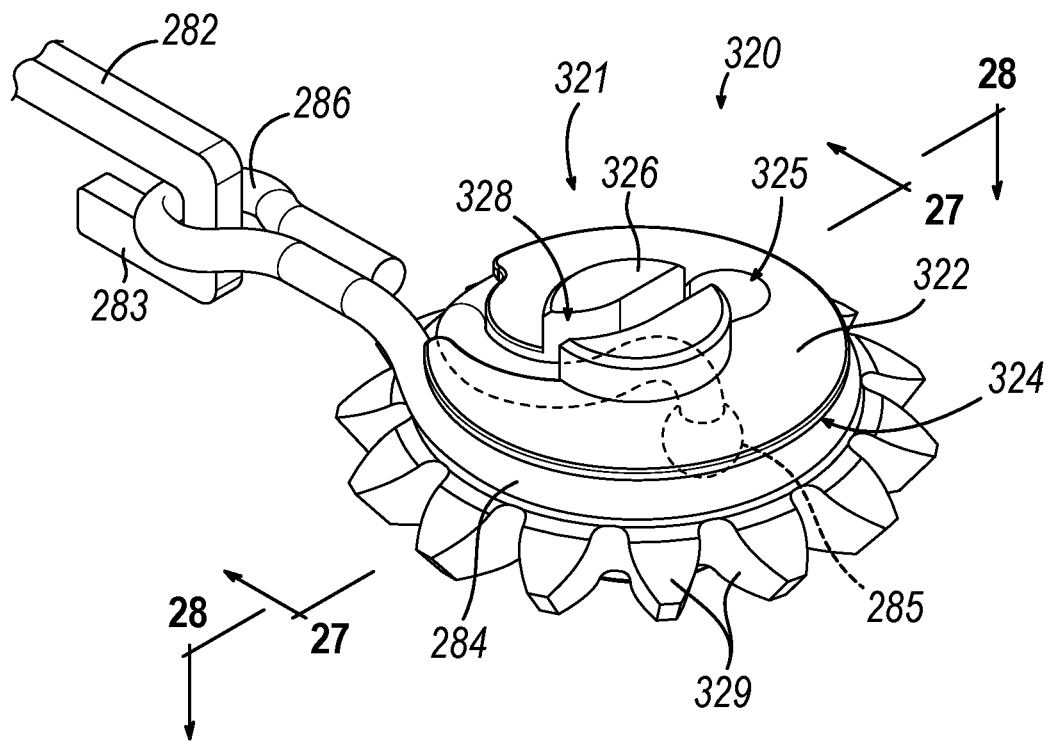
FIG. 26 depicts a perspective view of a fifth example of a rotation driver assembly with a fourth exemplary pulley and gear assembly that may be readily incorporated into the distal shaft portion of FIG. 18A.
Figure 27:
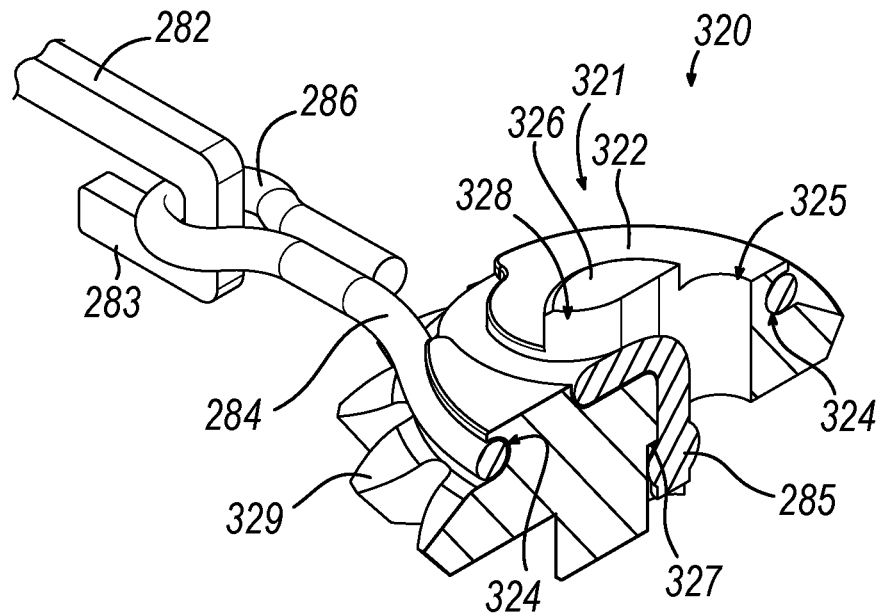
FIG. 27 depicts a sectional perspective view of the pulley and gear assembly of FIG. 26, taken along section line 27-27 of FIG. 26.
Figure 28:
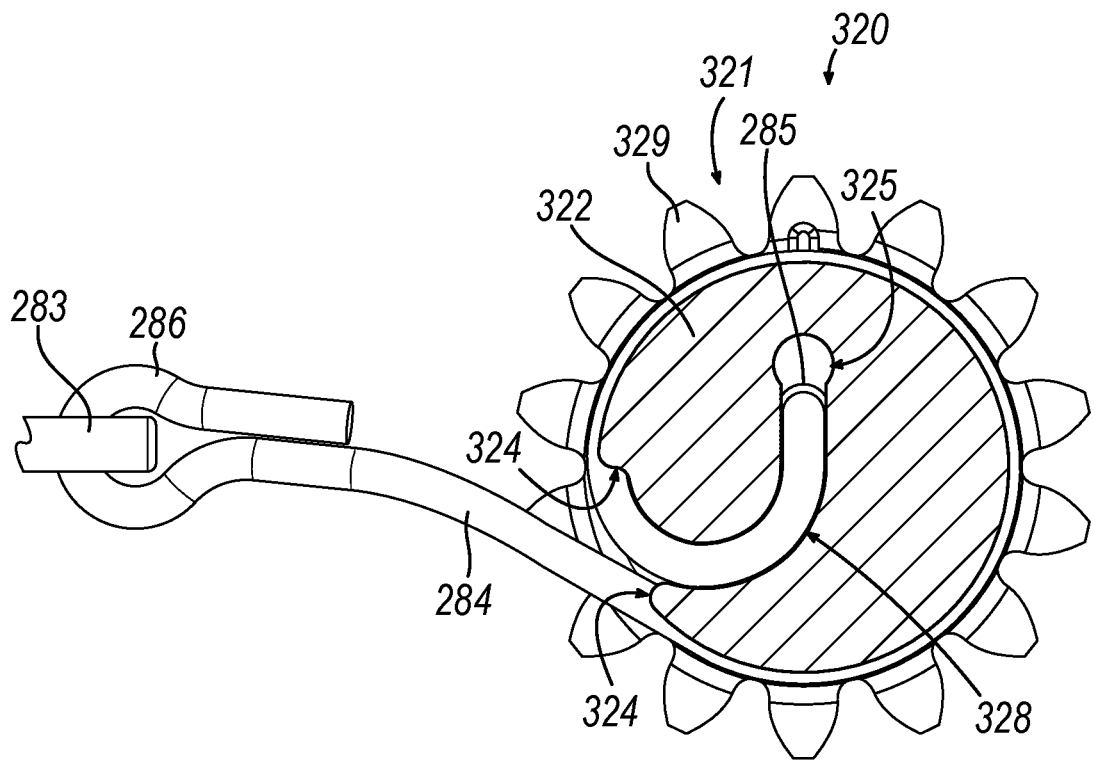
FIG. 28 depicts a cross-sectional view of the pulley and gear assembly of FIG. 26, taken along section line 28-28 of FIG. 26.

FIGS. 26-28 show a fifth example of a rotation driver assembly (321) including a fourth exemplary pulley and gear assembly (320) that may be readily incorporated into clamp arm clocking assembly (280) in replacement of pulley and gear assembly (290) described above. Pulley and gear assembly (320) is substantially similar to pulley and gear assembly (300) described above, except that rather than a top opening (305), pulley and gear assembly (320) defines an keyed opening (325) configured to receive distal ball (285) such that distal ball (285) abuts against a downwardly facing ledge (327).

Pulley and gear assembly (320) includes a pulley body (322), a central projection (326), and a gear (329); which may be substantially similar to pulley body (302), central projection (306), and gear (309) described above, respectively, with differences described below.

Pulley body (322) defines a cable recess (324) substantially similar to cable recess (304) described above. Pulley body (322) also defines coupling channel (328) extending between cable recess (324) and keyed opening (325). In the current example coupling channel (328) extends on pulley body (322) through central projection (326), rather than around central projection (316).

Similar to top opening (305) described above, a user may simply insert ball (285) into keyed opening (325). However, the user may insert ball (285) through keyed opening (325) into a lower recess at least partially defined by downwardly facing ledge (327) such that ball (285) abuts against ledge (327), thereby preventing ball (285) from being pulled out of the lower recess. Next, the user may then wrap cable (284) around cable recess (324) in accordance with the description herein. In other words, the user may couple cable (284) with pulley and gear assembly (320) without threading the proximal end of cable (284) through pulley and gear assembly (320). Therefore, the user may more easily attach cable (284) to pulley and gear assembly (320) after pulley and gear assembly (320) is attached to other components of instrument (200), such as translating body (164).

Figure 29:
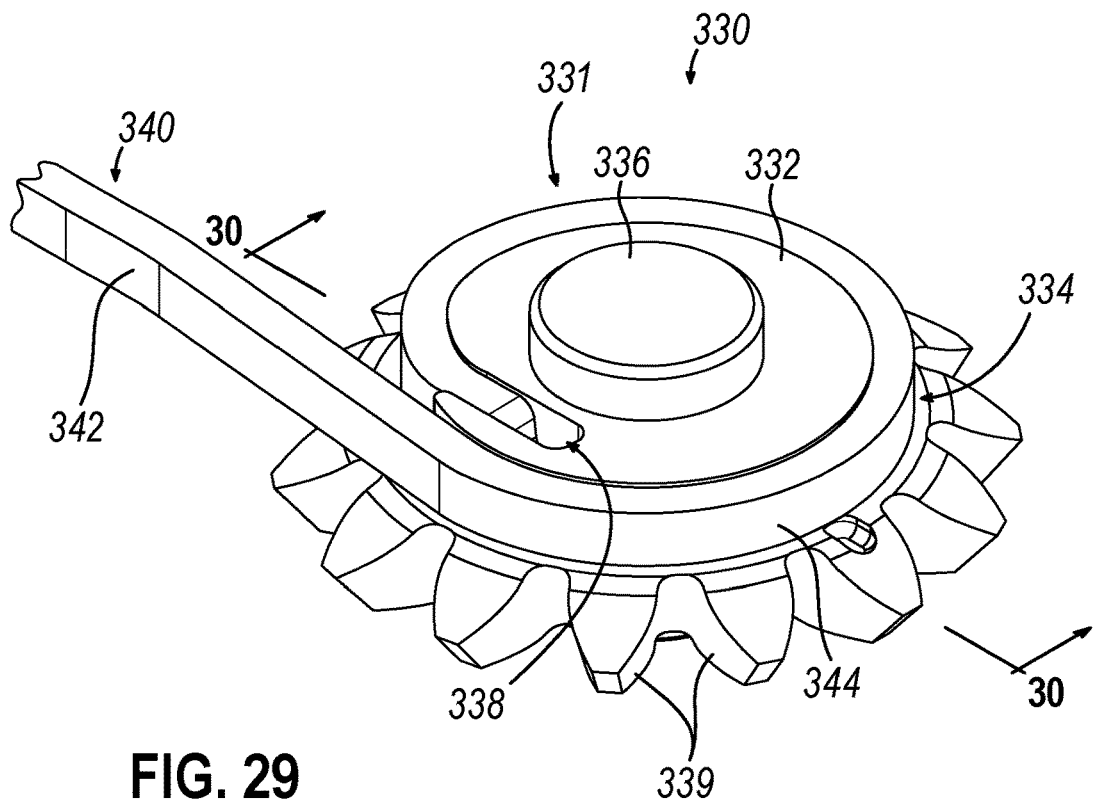
FIG. 29 depicts a perspective view of a sixth example of a rotation driver assembly with a fifth exemplary pulley and gear assembly that may be readily incorporated into the distal shaft portion of FIG. 18A.
Figure 30:
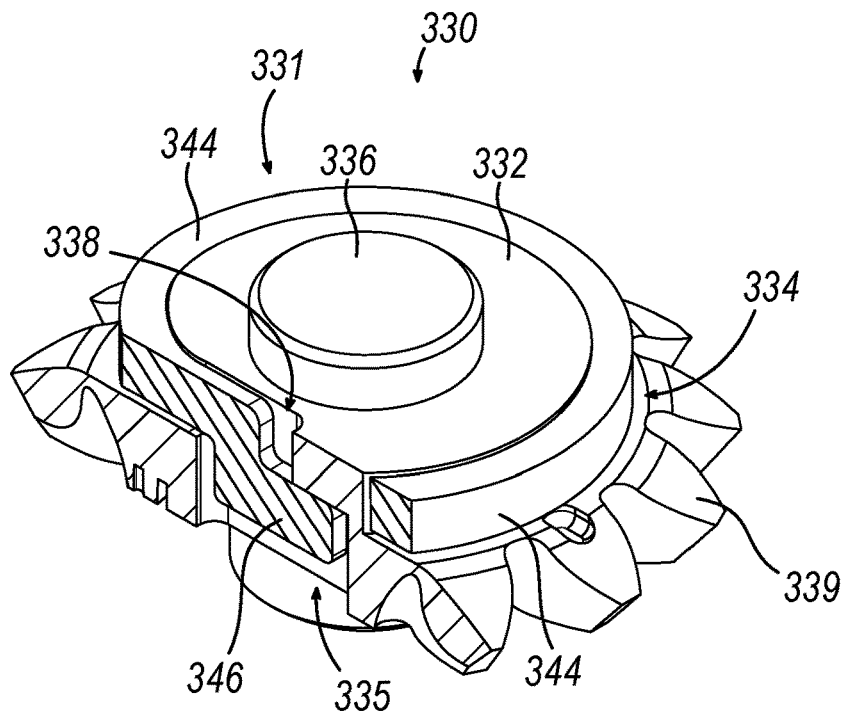
FIG. 30 depicts a sectional perspective view of the translating driver, and pulley and gear assembly, taken along section line 30-30 of FIG. 29.

FIGS. 29-30 show a sixth example of a rotation driver assembly (331) including a fifth exemplary pulley and gear assembly (330) and driver band (340) that may be readily incorporated into clamp arm clocking assembly (280) in replacement of pulley and gear assembly (290), translating driver (282), and cable (284) described above.

Pulley and gear assembly (330) is substantially similar to pulley and gear assembly (300) described above, except that rather than being configured to receive cable (284), a distal band portion (344) of translating driver (340) is wrapped around an exterior of pulley and gear assembly (330) such that distal band portion (344) is configured to rotate pulley and gear assembly (300) in response to proximal translation of translating driver (340). In other words, pulley and gear assembly (330) is configured to couple directly to translating driver (340), rather than require an intermediate cable.

Pulley and gear assembly (330) includes a pulley body (332), a central projection (336), and a gear (339); which may be substantially similar to pulley body (302), central projection (306), and gear (309) described above, respectively, with differences described below.

Pulley body (332) defines a band recess (334) dimensioned to receive distal band portion (344) such that distal band portion (344) wraps around band recess (334). Pulley body (332) also defines coupling channel (328) extending between band recess (334) and an interior recess (335) dimensioned to contain a distal coupling body (346) of translating driver (340). When pulley and gear assembly (330) and translating driver (340) are suitably coupled together, distal coupling body (346) is contained within interior recess (335) in order to prevent distal band portion (344) from disassociating with pulley body (332).

Distal band portion (344) may be made out of a suitable material such that as translating driver (340) rotates pulley and gear assembly (330), distal band portion (344) continues to sufficiently engage pulley body (332). In some instances, distal band portion (344) is made from a different material than proximal band portion (342). Distal band portion (344) may be formed from a shape memory material such that as proximal band portion (342) is driven distally, distal band portion (344) suitably rewraps around pulley body (332) defining band recess (334).

In some instances, frictional engagement between distal band portion (344) and pulley body (332) defining band recess (334) is sufficient to rotate pulley and gear assembly (330) in response to proximal translation of proximal band portion (342). In some instances, engagement between distal coupling body (346) and the portion of pulley body (332) defining interior recess (335) is sufficient to rotate pulley and gear assembly (330) in response to proximal translation of proximal band portion (342).

Figure 31:
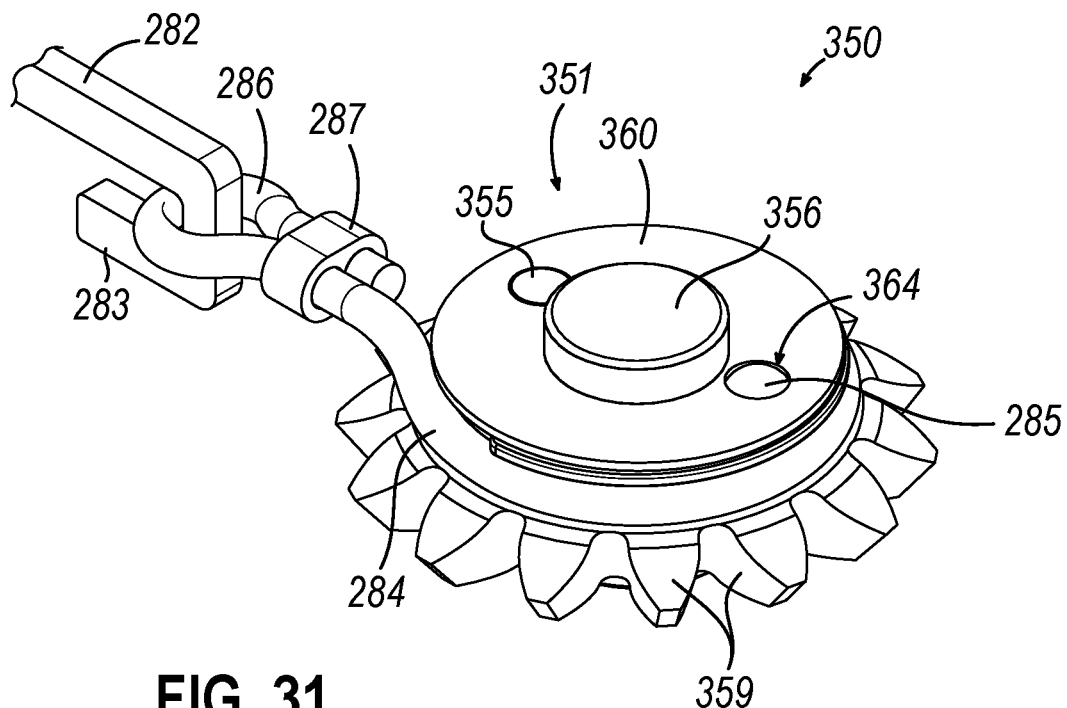
FIG. 31 depicts a perspective view of a seventh example of a rotation driver assembly with a sixth exemplary pulley and gear assembly that may be readily incorporated into the distal shaft portion of FIG. 18A.
Figure 32:
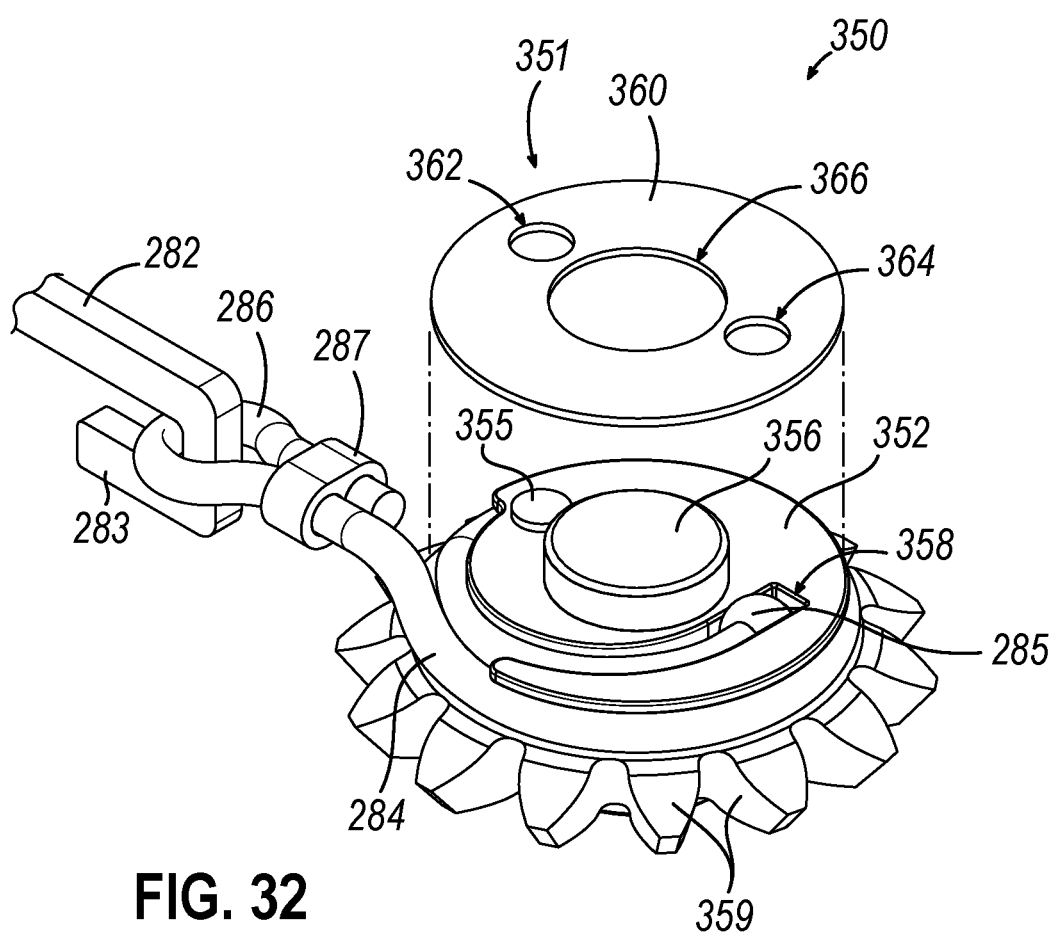
FIG. 32 depicts a partially exploded perspective view of the pulley and gear assembly of FIG. 31.

FIGS. 31-32 show a seventh example of a rotation driver assembly (351) including a sixth exemplary pulley and gear assembly (350) that may be readily incorporated into clamp arm clocking assembly (280) in replacement of pulley and gear assembly (290) described above. Pulley and gear assembly (350) is substantially similar to pulley and gear assembly (310) described above, except that pulley and gear assembly (350) includes a cap (360) configured to keep cable (284) retained within pulley body (352).

Pulley and gear assembly (350) includes a pulley body (352), a central projection (356), and a gear (359); which may be substantially similar to pulley body (302), central projection (306), and gear (309) described above, respectively, with differences described below.

Pulley body (352) defines a cable recess (354) substantially similar to cable recess (304) described above. Pulley body (352) also defines coupling channel (358) dimensioned to receive a portion of cable (284) and distal ball (285). Pulley body (352) also includes a coupling projection (355) dimensioned to help couple cap (360) to pulley body (352). Cap (360) defines a first recess (362), a second recess (364), and a central recess (366). Recesses (362, 364, 366) are dimensioned to fit over projections (355, 356) and distal ball (285), respectively, in order to couple cap (360) with both pulley body (352) and cable (284). Therefore, cap (360) may help keep cable (284) attached to pulley body (352). Cap (360) may couple with pulley body (352) and distal ball (285) through any suitable means as would be apparent to one skilled in the art in view of the teachings herein. For instance, cap (360) may couple with pulley body (352) and distal ball (285) via a press-fitting, friction fitting, adhesives, etc.

A user may simply insert ball (285) into coupling channel (358) and attach cap (360) to secure cable (284) to pulley body (352). Next, the user may wrap cable (284) around cable recess (354) in accordance with the description herein. In other words, the user may couple cable (284) with pulley and gear assembly (350) without threading the proximal end of cable (284) through pulley and gear assembly (350). Therefore, the user may more easily attach cable (284) to pulley and gear assembly (350) after pulley and gear assembly (350) is attached to other components of instrument (200), such as translating body (164).

Additionally, in the current example, there is an attachment feature (287) coupled to the proximal end of cable (284) in order to help form loop (286). Attachment feature (287) may be used on any example when loop (286) is formed.

Figure 33:
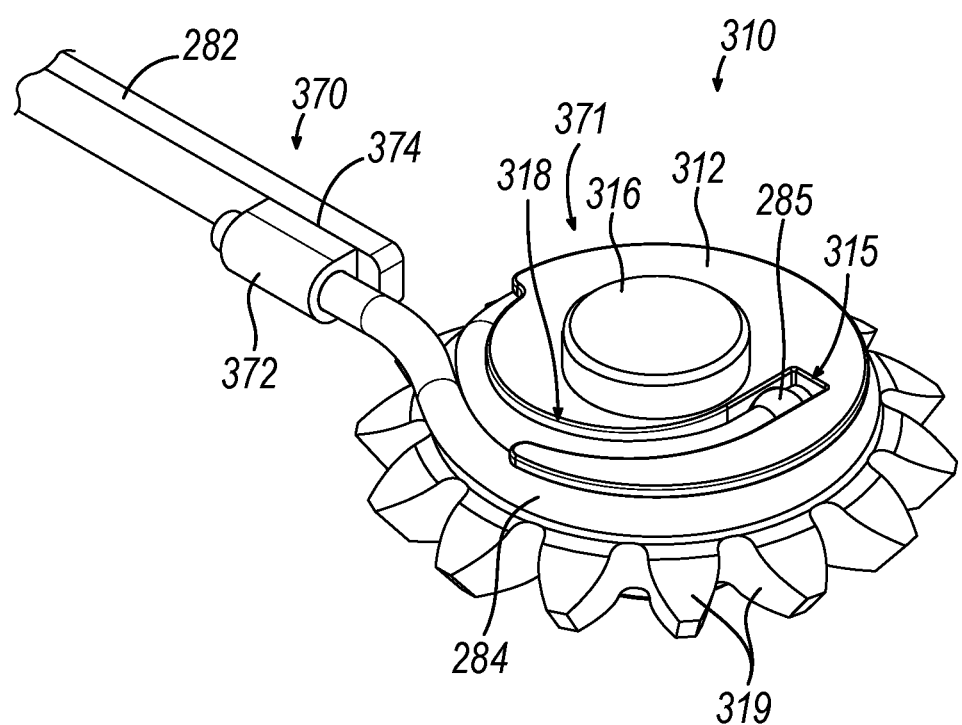
FIG. 33 depicts a perspective view of an eighth example of a rotation driver assembly with the pulley and gear assembly of FIG. 31 and a welded assembly that may be readily incorporated into the distal shaft portion of FIG. 18A.

As mentioned above, cable (284) may be coupled to translating driver (282) via any suitable means as would be apparent to one skilled in the art in view of the teachings herein. FIG. 33 shows an eighth example of a rotation driver assembly (371) including pulley and gear assembly (310) with cable (284) coupled to translating driver (282) via a welded assembly (370) rather than a hook and loop assembly. Welded assembly (370) includes a welded body (372) fixed to a proximal end of cable (284). Welded body (372) is fixedly attached to a distal end of translating driver (282) at a weld point (374). Since cable (284) is fixed to welded body (372), and welded body (372) is fixed to translating driver (282), cable (284) is fixed to translating driver (282). Welded body (372) may be coupled to translating driver (282) and cable (284) at any suitable time during assembly.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) an end effector, comprising: (i) an ultrasonic blade, and (ii) a clamp arm configured to move relative to the ultrasonic blade between an open position and a closed position; (b) an articulation section located proximally relative to the end effector, wherein the articulation section is configured to deflect the end effector between a non-articulated configuration and an articulated configuration; (c) an acoustic waveguide comprising a distal portion coupled to the ultrasonic blade, wherein the distal portion extends along an axis; (d) a clamp arm closure assembly comprising a body extending distally from the articulation section, wherein the body is configured to actuate in order to drive the clamp arm between the open position and the closed position; and (e) a clamp arm clocking assembly configured to drive rotation of the clamp arm about the axis relative to the ultrasonic blade between a first clocked position and a second clocked position, the clamp arm clocking assembly comprising: (i) a rotating body configured to rotate relative to the ultrasonic blade about the axis, wherein the clamp arm is pivotally coupled to the rotating body, (ii) a translating driver extending through the articulation section, and (iii) a rotation driver assembly in communication with the translating driver and the rotating body, wherein the rotation driver assembly is configured to convert translational motion of the translating driver into rotational motion of the rotating body to drive the clamp arm between the first clocked position and the second clocked position.

Example 2

The surgical instrument of claim 1, wherein the rotating body comprises an annular array of proximally presented gear teeth.

Example 3

The surgical instrument of any one or more of the preceding Examples, wherein the rotation driver assembly comprises a first gear that meshes with the annular array of proximally presented gear teeth of the rotating body.

Example 4

The surgical instrument of any one or more of the preceding Examples, wherein the rotation driver assembly further comprises a rack coupled to a distal end of the translating driver.

Example 5

The surgical instrument of any one or more of the preceding Examples, wherein the rotation driver assembly further comprises a second gear fixed to the first gear, wherein the second gear meshes with the rack.

Example 6

The surgical instrument of any one or more of the preceding Examples, wherein the rotation driver assembly further comprises a pulley fixed to the first gear.

Example 7

The surgical instrument of any one or more of the preceding Examples, wherein the rotation driver assembly further comprises a cable extending between the pulley and the translating driver.

Example 8

The surgical instrument of any one or more of the preceding Examples, wherein the cable extends through a channel extending into a central projection of the pulley.

Example 9

The surgical instrument of any one or more of the preceding Examples, wherein the channel extends through a bottom side of the central projection.

Example 10

The surgical instrument of any one or more of the preceding Examples, wherein the channel terminates on a top side of the central projection.

Example 11

The surgical instrument of any one or more of the preceding Examples, wherein the channel defines a keyhole.

Example 12

The surgical instrument of any one or more of the preceding Examples, where the cable extends through a channel extending around a central projection of the pulley.

Example 13

The surgical instrument of any one or more of the preceding Examples, further comprising a cap configured to couple the cable with the pulley.

Example 14

The surgical instrument of any one or more of the preceding Examples, wherein a distal end of the translating driver wraps around the pulley.

Example 15

The surgical instrument of any one or more of the preceding Examples, wherein the rotating body comprises a distally projecting tongue pivotally connected to the clamp arm.

Example 16

A surgical instrument, comprising: (a) an end effector, comprising: (i) an ultrasonic blade, and (ii) a clamp arm configured to move relative to the ultrasonic blade between an open position and a closed position; (b) an articulation section located proximally relative to the end effector, wherein the articulation section is configured to deflect the end effector between a non-articulated configuration and an articulated configuration; (c) a distal shaft portion extending distally from the articulation section along an axis; (d) a clamp arm closure assembly configured to drive the clamp arm between the open position and the closed position; and (e) a clamp arm clocking assembly configured to drive rotation of the clamp arm about the axis relative to the ultrasonic blade between a first clocked position and a second clocked position, the clamp arm clocking assembly comprising: (i) a rotating body configured to rotate relative to the ultrasonic blade about the axis, wherein the clamp arm is pivotally coupled to the rotating body, and (ii) a drive assembly at least partially extending through the articulation section, wherein the drive assembly is configured to convert translational motion into rotational motion of the rotating body.

Example 17

The surgical instrument of any one or more of the preceding Examples, wherein the drive assembly comprises a rack and a compound gear.

Example 18

The surgical instrument of any one or more of the preceding Examples, wherein the drive assembly comprises a cable and pulley system.

Example 19

A surgical instrument, comprising: (a) an end effector, comprising: (i) an ultrasonic blade, and (ii) a clamp arm configured to move relative to the ultrasonic blade between an open position and a closed position; (b) an articulation section located proximally relative to the end effector, wherein the articulation section is configured to deflect the end effector between a non-articulated configuration and an articulated configuration; (c) a distal shaft portion extending distally from the articulation section along an axis; and (d) a clamp arm clocking assembly configured to drive rotation of the clamp arm about the axis relative to the ultrasonic blade between a first clocked position and a second clocked position, the clamp arm clocking assembly comprising: (i) a rotating body configured to rotate relative to the ultrasonic blade about the axis, wherein the clamp arm is pivotally coupled to the rotating body, and (ii) a drive assembly comprising: (A) a driver at least partially extending through the articulation section, and (B) a rotation driver assembly configured to convert translational motion of the driver into rotational motion of the rotating body.

Example 20

The surgical instrument of any one or more of the preceding Examples, wherein the rotation driver assembly comprises a cable attached to a distal end of the driver.

V. Miscellaneous

Any one or more of the teaching, expressions, embodiments, examples, etc. described herein may be combined with any one or more of the teachings, expressions, embodiments, examples, etc. described in U.S. patent application Ser. No. 16/556,661, entitled "Ultrasonic Surgical Instrument with a Multi-Planar Articulating Shaft Assembly," filed on Aug. 30, 2019, issued as U.S. Pat. No. 11,690,642 on Jul. 4, 2023; U.S. patent application Ser. No. 16/556,667, entitled "Ultrasonic Transducer Alignment of an Articulating Ultrasonic Surgical Instrument," filed on Aug. 30, 2019, issued as U.S. Pat. No. 11,612,409 on Mar. 28, 2023; U.S. patent application Ser. No. 16/556,625, entitled "Ultrasonic Surgical Instrument with Axisymmetric Clamping," filed on Aug. 30, 2019, issued as U.S. Pat. No. 11,471,181 on Oct. 18, 2022; U.S. patent application Ser. No. 16/556,635, entitled "Ultrasonic Blade and Clamp Arm Alignment Features," filed on Aug. 30, 2019, issued as U.S. Pat. No. 11,457,945 on Oct. 4, 2022; U.S. patent application Ser. No.

16/556,727, entitled "Rotatable Linear Actuation Mechanism," filed on Aug. 30, 2019, issued as U.S. Pat. No. 11,712,261 on Aug. 1, 2023; U.S. patent application Ser. No. 17/077,067, entitled "Surgical Instrument and Carrier KART Supporting Ultrasonic Transducer," filed on Oct. 22, 2020, published as U.S. Pub. No. 2022/0125465 on Apr. 28, 2022, issued as U.S. Pat. No. 12,035,935 on Jul. 16, 2024; U.S. patent application Ser. No. 17/077,086, entitled "Carrier KART and Jaw Closure of an Ultrasonic Surgical Instrument," filed on Oct. 22, 2020, published as U.S. Pub. No. 2022/0125466 on Apr. 28, 2022, issued as U.S. Pat. No. 12,016,587 on Jun. 25, 2024; U.S. patent application Ser. No. 17/077,130, entitled "Surgical Instrument with Clamping Sensor Feedback and Related Methods," filed on Oct. 22, 2020, published as U.S. Pub. No. 2022/0125469 on Apr. 28, 2022; U.S. patent application Ser. No. 17/077,136, entitled "Surgical Instrument with Non-clamping Sensor Feedback and Related Methods," filed on Oct. 22, 2020, published as U.S. Pub. No. 2022/0125470 on Apr. 28, 2022, issued as U.S. Pat. No. 11,950,798 on Apr. 9, 2024; U.S. patent application Ser. No. 17/077,250, entitled "Ultrasonic Surgical Instrument with a Carrier KART and Reusable Stage," filed on Oct. 22, 2020, published as U.S. Pub. No. 2022/0125472 on Apr. 28, 2022, issued as U.S. Pat. No. 11,998,228 on Jun. 4, 2024; U.S. patent application Ser. No. 17/077,373, entitled "Surgical Instrument with a Carrier KART and Various Communication Cable Arrangements," filed on Oct. 22, 2020, published as U.S. Pub. No. 2022/0125473 on Apr. 28, 2022, issued as U.S. Pat. No. 11,931,059 on Mar. 19, 2024; U.S. patent application Ser. No. 17/077,139, entitled "Ultrasonic Surgical Instrument with a Fixed Transducer Grounding," filed on Oct. 22, 2020, published as U.S. Pub. No. 2022/0125471 on Apr. 28, 2022; U.S. patent application Ser. No. 17/077,146, entitled "Ultrasonic Surgical Instrument with a Shaft Assembly and Elongated Waveguide Support Arrangement," filed on Oct. 22, 2020, published as U.S. Pub. No. 2022/0125460 on Apr. 28, 2022; U.S. patent application Ser. No. 17/077,152, entitled "Damping Rings for an Ultrasonic Surgical Instrument," filed on Oct. 22, 2020, issued as U.S. Pat. No. 11,806,037 on Nov. 7, 2023; U.S. patent application Ser. No. 17/077,110, entitled "Ultrasonic Surgical Instrument with a Mid-Shaft Closure System and Related Methods," filed on Oct. 22, 2020, published as U.S. Pub. No. 2022/0125468 on Apr. 28, 2022, issued as U.S. Pat. No. 11,944,341 on Apr. 2, 2024; U.S. patent application Ser. No. 17/076,956, entitled "Surgical Instrument with an Articulatable Shaft Assembly and Dual End Effector Roll," filed on Oct. 22, 2020, published as U.S. Pub. No. 2022/0125463 on Apr. 28, 2022, issued as U.S. Pat. No. 11,890,030 on Feb. 6, 2024; U.S. patent application Ser. No. 17/076,959, entitled "Ultrasonic Surgical Instrument with a Distally Grounded Acoustic Waveguide," filed on Oct. 22, 2020, published as U.S. Pub. No. 2022/0125464 on Apr. 28, 2022, issued as U.S. Pat. No. 11,998,227 on Jun. 4, 2024; and/or U.S. patent application Ser. No. 17/077,098, entitled "Ultrasonic Surgical Instrument with a Multiplanar Articulation Joint," filed on Oct. 22, 2020, published as U.S. Pub. No. 2022/0125467 on Apr. 28, 2022, now abandoned. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A surgical instrument, comprising:
 (a) an end effector, including:
  (i) an ultrasonic blade, and
  (ii) a clamp arm configured to move relative to the ultrasonic blade between an open position and a closed position;
 (b) an acoustic waveguide including a distal portion coupled to the ultrasonic blade, wherein the distal portion extends along an axis;
 (c) a clamp arm closure assembly configured to actuate in order to drive the clamp arm between the open position and the closed position; and
 (d) a clamp arm clocking assembly configured to drive rotation of the clamp arm about the axis relative to the ultrasonic blade between a first clocked position and a second clocked position, the clamp arm clocking assembly including:
(i) a rotating body rotatably connected to the clamp arm closure assembly and configured to rotate relative to the ultrasonic blade about the axis, wherein the clamp arm is pivotally coupled to the rotating body,
(ii) a first translating driver configured to selectively translate relative to the clamp arm closure assembly, and
(iii) a first rotation driver assembly including a first rotation driver rotatably connected to the clamp arm closure assembly and operatively connected between the rotating body and the first translating driver, wherein the first rotation driver assembly is configured to convert translational motion of the first translating driver into rotational motion of the rotating body to drive the clamp arm between the first clocked position and the second clocked position,
wherein the rotating body is configured to rotate about a first axis, wherein the first rotation driver is configured to rotate about a second axis, and wherein the first axis is perpendicular to the second axis.

2. The surgical instrument of claim 1, wherein the clamp arm closure assembly with the rotating body and the first rotation driver rotatably connected thereto are configured to selectively translate along the axis in order to drive the clamp arm between the open position and the closed position.

3. The surgical instrument of claim 1, further comprising an articulation section located proximally relative to the end effector, wherein the articulation section is configured to deflect the end effector between a non-articulated configuration and an articulated configuration.

4. The surgical instrument of claim 3, wherein the first translating driver extends through the articulation section.

5. The surgical instrument of claim 1, wherein the rotating body includes a distally projecting tongue pivotally connected to the clamp arm.

6. The surgical instrument of claim 1, wherein the acoustic waveguide has a pin extending therethrough, and wherein the clamp arm closure assembly includes an elongate slot, and wherein the elongate slot receives the pin within the elongate slot.

7. The surgical instrument of claim 1, wherein the clamp arm clocking assembly further includes:
(i) a second translating driver configured to selectively translate relative to the clamp arm closure assembly, and
(iii) a second rotation driver assembly including a second rotation driver rotatably connected to the clamp arm closure assembly and operatively connected between the rotating body and the second translating driver, wherein second the rotation driver assembly is configured to convert translational motion of the second translating driver into rotational motion of the rotating body to drive the clamp arm between the first clocked position and the second clocked position.

8. The surgical instrument of claim 1, wherein the rotating body includes an array of proximally presented gear teeth, and wherein the first rotation driver includes a first gear that meshes with the array of proximally presented gear teeth of the rotating body.

9. The surgical instrument of claim 8, wherein the first rotation driver assembly further comprises a rack coupled to a distal end of the first translating driver.

10. The surgical instrument of claim 1, wherein the first rotation driver assembly further includes a pulley fixed to the first rotation driver.

11. The surgical instrument of claim 10, wherein the first rotation driver assembly further includes a cable extending between the pulley and the first translating driver.

12. The surgical instrument of claim 11, wherein the cable extends through a channel extending into a central projection of the pulley.

13. The surgical instrument of claim 11, where the cable extends through a channel extending around a central projection of the pulley.

14. The surgical instrument of claim 10, wherein a distal end of the first translating driver wraps around the pulley.

15. A surgical instrument, comprising:
(a) an end effector, including:
(i) an ultrasonic blade, and
(ii) a clamp arm configured to move relative to the ultrasonic blade between an open position and a closed position;
(b) an acoustic waveguide including a distal portion coupled to the ultrasonic blade, wherein the distal portion extends along an axis;
(c) a clamp arm closure assembly configured to actuate in order to drive the clamp arm between the open position and the closed position; and
(d) a clamp arm clocking assembly configured to drive rotation of the clamp arm about the axis relative to the ultrasonic blade between a first clocked position and a second clocked position, the clamp arm clocking assembly including:
(i) a rotating body rotatably connected to the clamp arm closure assembly and configured to rotate relative to the ultrasonic blade about the axis, wherein the clamp arm is pivotally coupled to the rotating body,
(ii) a first translating driver configured to selectively translate relative to the clamp arm closure assembly,
(iii) a first rotation driver assembly including a first rotation driver rotatably connected to the clamp arm closure assembly and operatively connected between the rotating body and the first translating driver, wherein the first rotation driver assembly is configured to convert translational motion of the first translating driver into rotational motion of the rotating body to drive the clamp arm between the first clocked position and the second clocked position,
(iv) a second translating driver configured to selectively translate relative to the clamp arm closure assembly, and
(v) a second rotation driver assembly including a second rotation driver rotatably connected to the clamp arm closure assembly and operatively connected between the rotating body and the second translating driver, wherein second the rotation driver assembly is configured to convert translational motion of the second translating driver into rotational motion of the rotating body to drive the clamp arm between the first clocked position and the second clocked position.

16. A surgical instrument, comprising:
(a) an end effector, including:
(i) an ultrasonic blade, and
(ii) a clamp arm configured to move relative to the ultrasonic blade between an open position and a closed position;

(b) an acoustic waveguide including a distal portion coupled to the ultrasonic blade, wherein the distal portion extends along an axis;

(c) a clamp arm closure assembly configured to actuate in order to drive the clamp arm between the open position and the closed position; and (d) a clamp arm clocking assembly configured to drive rotation of the clamp arm about the axis relative to the ultrasonic blade between a first clocked position and a second clocked position, the clamp arm clocking assembly including:

(i) a rotating body rotatably connected to the clamp arm closure assembly and configured to rotate relative to the ultrasonic blade about the axis, wherein the clamp arm is pivotally coupled to the rotating body, (ii) a first translating driver configured to selectively translate relative to the clamp arm closure assembly, and (iii) a first rotation driver assembly including a first rotation driver rotatably connected to the clamp arm closure assembly and operatively connected between the rotating body and the first translating driver, wherein the first rotation driver assembly is configured to convert translational motion of the first translating driver into rotational motion of the rotating body to drive the clamp arm between the first clocked position and the second clocked position, wherein the acoustic waveguide has a pin extending therethrough, and wherein the clamp arm closure assembly includes an elongate slot, and wherein the elongate slot receives the pin within the elongate slot.

17. The surgical instrument of claim 16, wherein the clamp arm closure assembly with the rotating body and the first rotation driver rotatably connected thereto are configured to selectively translate along the axis in order to drive the clamp arm between the open position and the closed position.

18. The surgical instrument of claim 17, further comprising an articulation section located proximally relative to the end effector, wherein the articulation section is configured to deflect the end effector between a non-articulated configuration and an articulated configuration.

19. The surgical instrument of claim 18, wherein the first translating driver extends through the articulation section.

20. The surgical instrument of claim 19, wherein the rotating body includes a distally projecting tongue pivotally connected to the clamp arm.

* * * * *